United States Patent
Gill et al.

(10) Patent No.: US 7,297,114 B2
(45) Date of Patent: Nov. 20, 2007

(54) SYSTEM AND METHOD FOR DISTINGUISHING AMONG CARDIAC ISCHEMIA, HYPOGLYCEMIA AND HYPERGLYCEMIA USING AN IMPLANTABLE MEDICAL DEVICE

(75) Inventors: Jong Gill, Valencia, CA (US); Peter Boileau, Valencia, CA (US); Rupinder Bharmi, Stevenson Ranch, CA (US); Xiaoyi Min, Thousand Oaks, CA (US); Joseph J. Florio, La Canada, CA (US); Michael Benser, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 297 days.

(21) Appl. No.: 11/043,804

(22) Filed: Jan. 25, 2005

(65) Prior Publication Data

US 2006/0167519 A1 Jul. 27, 2006

(51) Int. Cl.
*A61B 5/0452* (2006.01)
(52) U.S. Cl. ...................... 600/365; 600/513
(58) Field of Classification Search .......... 600/301, 600/365, 513, 516, 517; 607/22, 3
See application file for complete search history.

(56) References Cited

U.S. PATENT DOCUMENTS

| | | | |
|---|---|---|---|
| 4,731,051 A | 3/1988 | Fischell | 604/67 |
| 4,947,845 A | 8/1990 | Davis | 128/637 |
| 5,113,869 A | 5/1992 | Nappholz et al. | 128/696 |
| 5,135,004 A | 8/1992 | Adams et al. | 128/696 |
| 5,199,428 A | 4/1993 | Obel et al. | 128/419 C |
| 5,203,326 A | 4/1993 | Collins | 128/419 PG |
| 5,313,953 A | 5/1994 | Yomtov et al. | 128/696 |
| 5,365,426 A | 11/1994 | Siegel et al. | 364/413.06 |
| 5,520,191 A | 5/1996 | Karlsson et al. | 128/702 |
| 5,741,211 A | 4/1998 | Renirie et al. | 600/300 |
| 5,891,047 A | 4/1999 | Lander et al. | 600/516 |
| 5,960,797 A | 10/1999 | Kramer et al. | 128/899 |
| 6,016,443 A | 1/2000 | Ekwall et al. | 600/519 |
| 6,021,350 A | 2/2000 | Mathson | 607/17 |
| 6,038,469 A | 3/2000 | Karlsson et al. | 600/512 |

(Continued)

FOREIGN PATENT DOCUMENTS

| | | |
|---|---|---|
| EP | 0 939 602 B1 | 9/2004 |
| WO | WO97/15227 | 1/1997 |

OTHER PUBLICATIONS

Eckert, Bodil, et al. "Hypoglycaemia Leads to an Increased QT Interval in Normal Men," *Clinical Physiology*, May 1998; vol. 18, No. 6, pp. 570-575.

(Continued)

*Primary Examiner*—Kennedy Schaetzle

(57) ABSTRACT

Techniques are described for detecting ischemia, hypoglycemia or hyperglycemia based on intracardiac electrogram (IEGM) signals. Ischemia is detected based on a shortening of the interval between the QRS complex and the end of a T-wave (QTmax), alone or in combination with a change in ST segment elevation. Alternatively, ischemia is detected based on a change in ST segment elevation combined with minimal change in the interval between the QRS complex and the end of the T-wave (QTend). Hypoglycemia is detected based on a change in ST segment elevation along with a lengthening of either QTmax or QTend. Hyperglycemia is detected based on a change in ST segment elevation along with minimal change in QTmax and in QTend. By exploiting QTmax and QTend in combination with ST segment elevation, changes in ST segment elevation caused by hypo/hyperglycemia can be properly distinguished from changes caused by ischemia.

14 Claims, 15 Drawing Sheets

U.S. PATENT DOCUMENTS

| | | | |
|---|---|---|---|
| 6,108,577 A | 8/2000 | Benser | |
| 6,112,116 A | 8/2000 | Fischell et al. | 600/517 |
| 6,115,628 A | 9/2000 | Stadler et al. | 600/517 |
| 6,128,526 A | 10/2000 | Stadler et al. | 600/517 |
| 6,233,486 B1 | 5/2001 | Ekwall et al. | 607/17 |
| 6,256,538 B1 | 7/2001 | Ekwall | 607/17 |
| 6,264,606 B1 | 7/2001 | Ekwall et al. | 600/300 |
| 6,272,379 B1 | 8/2001 | Fischell et al. | 607/5 |
| 6,377,852 B1 | 4/2002 | Bornzin et al. | 607/9 |
| 6,381,493 B1 | 4/2002 | Stadler et al. | 607/9 |
| 6,501,983 B1 | 12/2002 | Natarajan et al. | 607/517 |
| 6,572,542 B1 | 6/2003 | Houben et al. | 600/300 |
| 7,016,720 B2 * | 3/2006 | Kroll | 600/513 |
| 7,029,443 B2 * | 4/2006 | Kroll | 600/365 |
| 7,103,412 B1 * | 9/2006 | Kroll | 607/17 |
| 2002/0143372 A1 | 10/2002 | Snell et al. | 607/30 |
| 2004/0077962 A1 | 4/2004 | Kroll | 600/513 |
| 2004/0138716 A1 | 7/2004 | Kon et al. | 607/17 |

OTHER PUBLICATIONS

Heller, Simon R., "Abnormalities of the Electrocardiogram During Hypoglycemia: The Cause of the Dead in Bed Syndrome?" *Int. J. Clin. Pract. Suppl. No. 129*, Jul. 2002, pp. 27-32.

Landstedt-Hallin, L., et al., "Increased QT Dispersion During Hypoglycaemia in Patients with Type 2 Diabetes Mellitus," *Journal of Internal Medicine*, 1999; vol. 246, pp. 299-307.

Jones, Timothy W., et al., "Mild Hypoglycemia and Impairment of Brain Stem and Cortical Evoked Potentials in Healthy Subjects," *Diabetes*, Dec. 1990; vol. 39, pp. 1550-1555.

Peterson, Karl-Georg, et al., "Regulation of Serum Potassium During Insulin-Induced Hypoglycemia," *Diabetes*, Jul. 1982; vol. 31, pp. 615-617.

Robinson, R.T.C.E., et al. "Changes in Cardiac Repolarization During Clinical Episodes of Nocturnal Hypoglycaemia in Adults with Type 1 Diabetes," *Diabetologia*, 2004; vol. 47, pp. 312-315.

Yanowitz, Frank G., MD, Prof. of Medicine, Univ. of Utah School of Medicine, "*Lesson X. ST Segment Abnormalities*," The Alan E. Lindsay—ECG Learning Center—In Cyberspace, 5 pages (http://medstat.med.utah.edu/kw/ecg/ecg_outline/Lesson10/).

Blendea, Mihaela C., MD, PhD, et al, "Heart Disease in Diabetic Patients" *Current Diabetes Reports*, 2003; vol. 3. pp. 223-229.

Malmberg, Klas for the DIGAMI Study Group, "Prospective Randomised Study of Intensive Insulin Treatment on Long-Term Survival After Acute Myocardial Infarction in Patients with Diabetes Mellitus", *BMJ*, May 24, 1997; vol. 314, pp. 1512-1515.

* cited by examiner

SYSTEM AND METHOD FOR DISTINGUISHING AMONG CARDIAC ISCHEMIA, HYPOGLYCEMIA AND HYPERGLYCEMIA USING AN IMPLANTABLE MEDICAL DEVICE

CROSS REFERENCE TO RELATED APPLICATIONS

This application is related to copending U.S. patent applications: 1) Ser. No. 11/043,612, titled "System and Method for Distinguishing Among Cardiac Ischemia, Hypoglycemia and Hyperglycemia Using an Implantable Medical Device"; and 2) Ser. No. 11/043,780, titled "System and Method for Distinguishing Among Cardiac Ischemia, Hypoglycemia and Hyperglycemia Using an Implantable Medical Device", all applications filed Jan. 25, 2005.

FIELD OF THE INVENTION

The invention generally relates to implantable medical devices such as pacemakers and implantable cardioverter/defibrillators (ICDs) and, in particular, to techniques for detecting cardiac ischemia, hypoglycemia and hyperglycemia using such devices.

BACKGROUND

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less. Accordingly, it would be highly desirable to provide a technique for reliably detecting acute myocardial ischemia so that the victim may be warned and medical attention sought. If properly warned, surgical procedures may be implemented to locate and remove the growing arterial blockage or anti-thrombolytic medications may be administered. At the very least, advanced warning would allow the victim to cease activities that might result in a fatal accident. Moreover, in many cases, AMI or VF is triggered by strenuous physical activities and so advanced warning would allow the victim to cease such activities, possibly preventing AMI or VF from occurring.

Many patients at risk of cardiac ischemia have pacemakers, ICDs or other medical devices implanted therein. Accordingly, techniques have been developed for detecting cardiac ischemia using implanted medical devices. In particular, techniques have been developed for analyzing intracardiac electrogram (IEGM) signals in an effort to detect cardiac ischemia. See, as examples, the following U.S. Pat. No. 5,113,869 to Nappholz; U.S. Pat. No. 5,135,004 to Adams et al.; U.S. Pat. No. 5,199,428 to Obel et al.; U.S. Pat. No. 5,203,326 to Collins; U.S. Pat. No. 5,313,953 to Yomtov et al; U.S. Pat. No. 6,501,983 to Natarajan, et al.; U.S. Pat. Nos. 6,016,443, 6,233,486, 6,256,538, and 6,264,606 to Ekwall; U.S. Pat. No. 6,021,350 to Mathson; U.S. Pat. Nos. 6,112,116 and 6,272,379 to Fischell et al; U.S. Pat. Nos. 6,128,526, 6,115,628 and 6,381,493 to Stadler et al; and U.S. Pat. No. 6,108,577 to Benser. Most IEGM-based ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). The QRS complex usually follows an atrial depolarization (also referred to as a P-wave.) Strictly speaking, P-waves, R-waves and T-waves are features of a surface electrocardiogram (EKG). For convenience and generality, herein the terms R-wave, T-wave and P-wave are used to refer to the corresponding internal signal component as well.

A significant concern with any cardiac ischemia detection technique that relies on changes in the ST segments is that systemic influences within the patient can alter the ST segment. For example, hypoglycemia (low blood sugar levels) and hyperglycemia (high blood sugar levels) can both affect ST segment deviation. In addition, electrolyte imbalance, such as hypokalemia (low potassium levels) or hyperkalemia (high potassium levels) can affect the ST segment. Certain anti-arrhythmic drugs can also affect the ST-segment.

Accordingly, alternative techniques for detecting cardiac ischemia have been developed, which do not rely on ST segment elevation. One such technique is set forth in U.S. patent application Ser. No. 10/603,429, entitled "System And Method For Detecting Cardiac Ischemia Using An Implantable Medical Device," of Wang et al., filed Jun. 24, 2003, which is incorporated by reference herein. Rather than examine the ST segment, the technique of Wang et al. instead examines post-T-wave segments, i.e. that portion of the cardiac signal immediately following the T-wave. In one example, the onset of cardiac ischemia is identified by detecting a sharp falling edge within post-T-wave signals. A warning is then provided to the patient. The warning preferably includes both a perceptible electrical notification signal applied directly to subcutaneous tissue and a separate warning signal delivered via short-range telemetry to a handheld warning device external to the patient. After the patient feels the internal warning signal, he or she holds the handheld device near the chest to receive the short-range telemetry signal, which provides a textual warning. The handheld warning device thereby provides confirmation of the warning to the patient, who may be otherwise uncertain as to the reason for the internally generated warning signal. Another technique for detecting cardiac ischemia based on T-waves is set forth in U.S. patent application Ser. No. 10/603,398, entitled "System And Method For Detecting Cardiac Ischemia Based On T-Waves Using An Implantable Medical Device," of Min et al., filed Jun. 24, 2003, which is also incorporated by reference herein. With the technique of Min et al., cardiac ischemia is detected based either on the total energy of the T-wave or on the maximum slope of the T-wave. Again, if ischemia is detected, a warning signal is provided to the patient.

Hence, various cardiac ischemia detection techniques have been developed that exploit T-waves. Although these techniques are effective, it would be desirable to provide still other T-wave-based ischemia detection techniques and it is to that end that aspects of the present invention are directed. It would also be desirable to provide techniques that exploit deviations in the ST segment as well as changes in T-waves to provide further improvements in cardiac ischemia detection. In particular, it would be highly desirable to identify particular changes in T-waves that can be used to distinguish deviations in the ST segment caused by cardiac ischemia from changes caused by hypoglycemia or hyperglycemia or other systemic affects so as to improve the reliability and specificity of ST segment-based ischemia detection. It is to this end that other aspects of the invention are directed.

Although the detection of cardiac ischemia is of paramount importance since an ischemia may be a precursor to a potentially fatal AMI or VF, it is also desirable to detect hypoglycemia or hyperglycemia so as to provide suitable warning signals and still other aspects of the invention are directed to that end. Diabetic patients, particular, need to frequently monitor blood glucose levels to ensure that the levels remain within acceptable bounds and, for insulin dependent diabetics, to determine the amount of insulin that must be administered. Conventional techniques for monitoring blood glucose levels, however, leave much to be desired. One conventional technique, for example, requires that the patient draw blood, typically by pricking the finger. The drawn blood is then analyzed by a portable device to determine the blood glucose level. The technique can be painful and therefore can significantly discourage the patient from periodically checking blood glucose levels. Moreover, since an external device is required to analyze the blood, there is the risk that the patient will neglect to keep the device handy, preventing periodic blood glucose level monitoring. For insulin-dependent diabetics, failure to properly monitor blood glucose levels can result in improper dosages of insulin causing, in extreme cases, severe adverse health consequences such as a ketoacidotic diabetic coma, which can be fatal. Accordingly, there is a significant need to provide a reliable hypo/hyperglycemia detection technique, which does not rely on the patient to monitoring his or her own glucose levels and which does not require an external analysis device.

In view of the many disadvantages of conventional external blood glucose monitoring techniques, implantable blood glucose monitors have been developed, which included sensors for mounting directly within the blood stream. However, such monitors have not achieved much success as the glucose sensors tend to clog over very quickly. Thus, an implantable device that could continually and reliably measure blood glucose levels without requiring glucose sensors would be very desirable. Moreover, as with any implantable device, there are attended risks associated with implanting the blood glucose monitor, such as adverse reactions to anesthetics employed during the implantation procedure or the onset of subsequent infections. Hence, it would be desirable to provide for automatic hypo/hyperglycemia detection using medical devices that would otherwise need to be implanted anyway, to thereby minimize the risks associated with the implantation of additional devices. In particular, for patients already requiring implantation of a cardiac stimulation device, such as a pacemaker or ICD, it would be desirable to exploit features of electrical cardiac signals, particularly ST segments and T-waves, for use in detecting hypo/hyperglycemia and still other aspects of the invention are directed to that end.

SUMMARY

In accordance with a first illustrative embodiment, various techniques are provided for use with an implantable medical device for detecting cardiac ischemia.

In a first exemplary cardiac ischemia detection technique, the device tracks changes over time in the length of an interval between the beginning of a QRS complex and the maximum amplitude (i.e. the peak) of a corresponding T-wave. This repolarization peak-based interval is referred to herein as QTmax. A change in the interval is referred to as ΔQTmax. The device detects the onset of myocardial ischemia based on any significant shortening of QTmax. A change in the length of QTmax is believed to be a reliable indicator of cardiac ischemia. Moreover, QTmax also provides a convenient means for distinguishing changes in the IEGM due to hyper/hypoglycemia from changes due to cardiac ischemia. Whereas cardiac ischemia causes a shortening of QTmax, hypoglycemia causes a lengthening. Hyperglycemia causes little or no change. Preferably, the device also exploits ST segment deviation to improve detection specificity. Cardiac ischemia typically causes a change in ST segment. Hence, if a significant deviation in the ST segment is detected along with a shortening of QTmax, the detection of cardiac ischemia based on QTmax is confirmed. Note that QRS complexes are electrical cardiac signals representative of depolarization or "activation" of the ventricles; whereas T-waves are electrical cardiac signals representative of repolarization or "deactivation" of the ventricles. Hence, a QRS complex is a ventricular depolarization event or a ventricular activation event. A T-wave is a ventricular repolarization event or a ventricular deactivation event. These alternative terms are used herein for generality where appropriate.

In a second exemplary cardiac ischemia detection technique, the device tracks changes over time in the ST segment and in the length of the interval between the beginning of a QRS complex and the end of a corresponding T-wave. This repolarization end-based interval is referred to herein as QTend. A change in the interval is referred to as ΔQTend. A change in the ST segment is referred to as ST deviation. The device then detects the onset of a myocardial ischemia based on any significant ST deviation occurring along with a lack of significant change in QTend, i.e. ΔQTend is nearly zero. In this regard, QTend provides a convenient means for distinguishing changes in the IEGM due to hypoglycemia from changes due to cardiac ischemia. Whereas cardiac ischemia causes little or no change in QTend, hypoglycemia causes a substantial lengthening of QTend. Hence, a significant ST deviation, which might otherwise be misinterpreted as an indication of ischemia, is instead properly interpreted as an indication of hypoglycemia if a substantial change in QTend is also observed. Hyperglycemia, on the other hand, causes a ST segment deviation but does not typically cause a significant change in QTend.

Preferably, the device tracks ST deviation and both QTmax and QTend to provide further specificity. A significant deviation in the ST segment combined with a shortening of QTmax and little or no change in QTend is indicative of cardiac ischemia. A significant deviation in the ST segment combined with a lengthening of both QTmax and QTend is indicative of hypoglycemia. A significant deviation in the ST segment combined with little or no change in QTmax and also little or no change in QTend is indicative of hyperglycemia. A lack of significant deviation in the ST segment indicates a lack of ischemia, hypoglycemia or hyperglycemia, i.e. that the patient is normal, at least insofar as these conditions are concerned. Accordingly, it may be preferable to first examine the ST segment before proceeding to examine QTmax and QTend.

In accordance with a second aspect of the invention, techniques are provided for use with an implantable medical device for detecting hypoglycemia. In an exemplary embodiment, the device tracks changes over time in QTmax and/or QTend. The device then detects the onset of a hypoglycemia based on any significant lengthening of QTmax and/or QTend. Preferably, the device also uses deviations in the ST segment to improve detection specificity. As noted, hypoglycemia typically causes a significant ST deviation. Hence, if a significant ST deviation is detected along with a lengthening of QTmax or QTend, the detection of hypoglycemia is confirmed. To provide increased specificity, ST deviation, QTmax and QTend are preferably all used. Otherwise conventional hypo/hyperglycemia detection parameters may be used as well to further optimize detection specificity/sensitivity.

In accordance with a third aspect of the invention, various techniques are provided for use with an implantable medical device for detecting hyperglycemia. In an exemplary embodiment, the device tracks deviations in the ST segment and in QTmax. The device then detects the onset of a hyperglycemia based on any significant ST deviation combined with little or no change in QTmax. As noted, hyperglycemia typically causes a significant deviation in the ST segment but causes little or no change in QTmax, whereas cardiac ischemia causes a significant deviation in the ST segment along with a significant reduction in QTmax. QTend may also be examined to provide corroboration. There is also little or no change in QTend during hyperglycemia.

The following table summarizes changes in the ST segment, QTmax and QTend in response to cardiac ischemia, hypoglycemia, and hyperglycemia that are exploited by the invention.

TABLE I

|  | ST Segment | QTmax | QTend |
| --- | --- | --- | --- |
| Ischemia | Significant deviation | Shortens | Little or no change |
| Hypoglycemia | Significant deviation | Lengthens | Lengthens |
| Hyperglycemia | Significant deviation | Little or no change | Little or no change |
| Normal | No significant deviation | No significant deviation | No significant deviation |

Upon detecting of the onset of an cardiac ischemia, hypoglycemia or hyperglycemia, appropriate warning signals are generated, which include both "tickle warning" signals applied to subcutaneous tissue and short range telemetry warning signals transmitted to a device external to the patient. In one example, once the tickle warning is felt, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal.

Therapy may also be initiated or modified. In this regard, pacing therapy may be modified in response to the detected medical condition or, if the device is equipped with a drug pump, appropriate medications may be administered. For ischemia, anti-thrombolytic drugs may be delivered. For hypo/hyperglycemia, insulin may be regulated. In addition, if the device is an ICD, it may be controlled to immediately begin charging defibrillation capacitors up on detection of ischemia so as to permit prompt delivery of a defibrillation shock, which may be needed if the ischemia triggers VF. Additionally, or in the alternative, values indicative of ST deviation, QTmax and/or QTend may be stored for diagnostic purposes. In this regard, the device may calculate an "ischemic burden", which is representative of the risk of ischemia and is derived from ST deviation, QTmax and/or QTend.

Hence, improved techniques are provided both for reliably detecting cardiac ischemia, hypoglycemia and hyperglycemia and for distinguishing therebetween. The techniques are preferably performed by the implanted medical device itself so as to provide prompt warnings of ischemia, hypoglycemia or hyperglycemia. Alternatively, the techniques may be performed by external devices, such as bedside monitors or the like, based on IEGM signals detected by an implanted device and transmitted to the external device.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
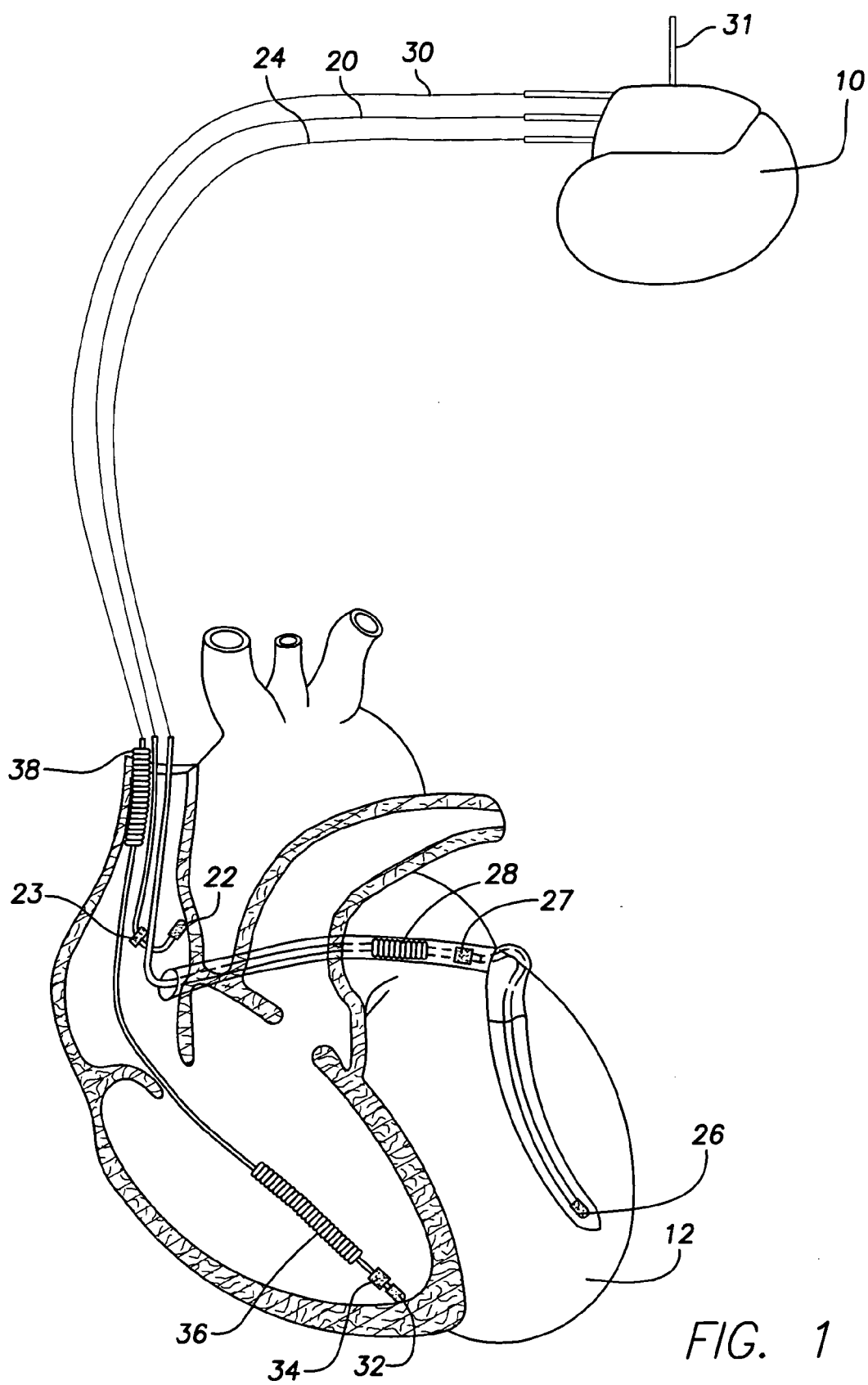
FIG. 1 is a simplified diagram illustrating an implantable stimulation device with at least three leads implanted in the heart of a patient for delivering multi-chamber stimulation and shock therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

Figure 2:
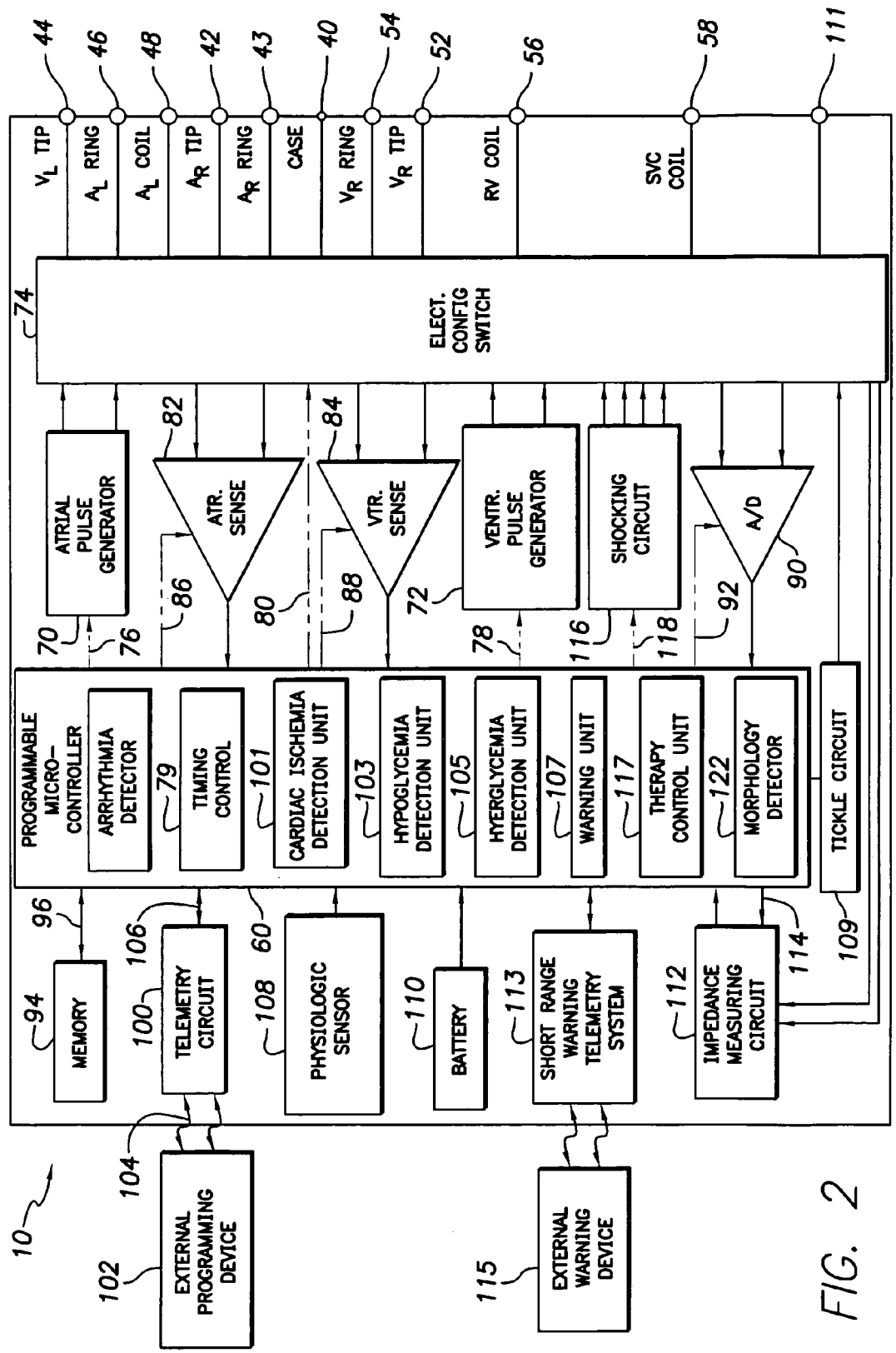
FIG. 2 is a functional block diagram of the implantable cardiac stimulation device of FIG. 1 illustrating basic elements of the stimulation device, particularly illustrating components for detecting cardiac ischemia, hypoglycemia, and hyperglycemia based on various combinations of QTmax, QTend and ST deviation.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. To provide the "tickle warning" signal, an additional terminal 59 is provided for connection to the tickle warning electrode 31 of FIG. 1.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112, which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Finally, with regard to FIG. 2, microcontroller 60 includes: a cardiac ischemia detection unit 101 for controlling the detection of episodes of cardiac ischemia; hypoglycemia detection-unit 103 for controlling the detection of episodes of hypoglycemia; and a hyperglycemia detection unit 105 for controlling the detection of episodes of hyperglycemia. A warning unit 107 controls delivery of warning signals to the patient indicative of ischemia, hypoglycemia, or hyperglycemia. In particular, warning unit 107 controls a tickle circuit 109 that generates subcutaneous perceptible warning signals via lead 31 (FIG. 1), which is connected via connector 111. Device case electrodes 40 may be used as the return electrode for the tickle warning signal. Thereafter, warning unit 107 controls a short-range telemetry system 113 to transmit warning signals to an external handheld warning device 115 for confirmation. Additionally, a therapy control unit 117 may be provided to control therapy based upon the detection of ischemia, hypoglycemia or hyperglycemia. The operation of these devices will be described below with reference to the remaining figures.

Referring to the remaining figures, flow charts, graphs and other diagrams illustrate the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Cardiac Ischemia Detection Based on QTmax

Figure 3:
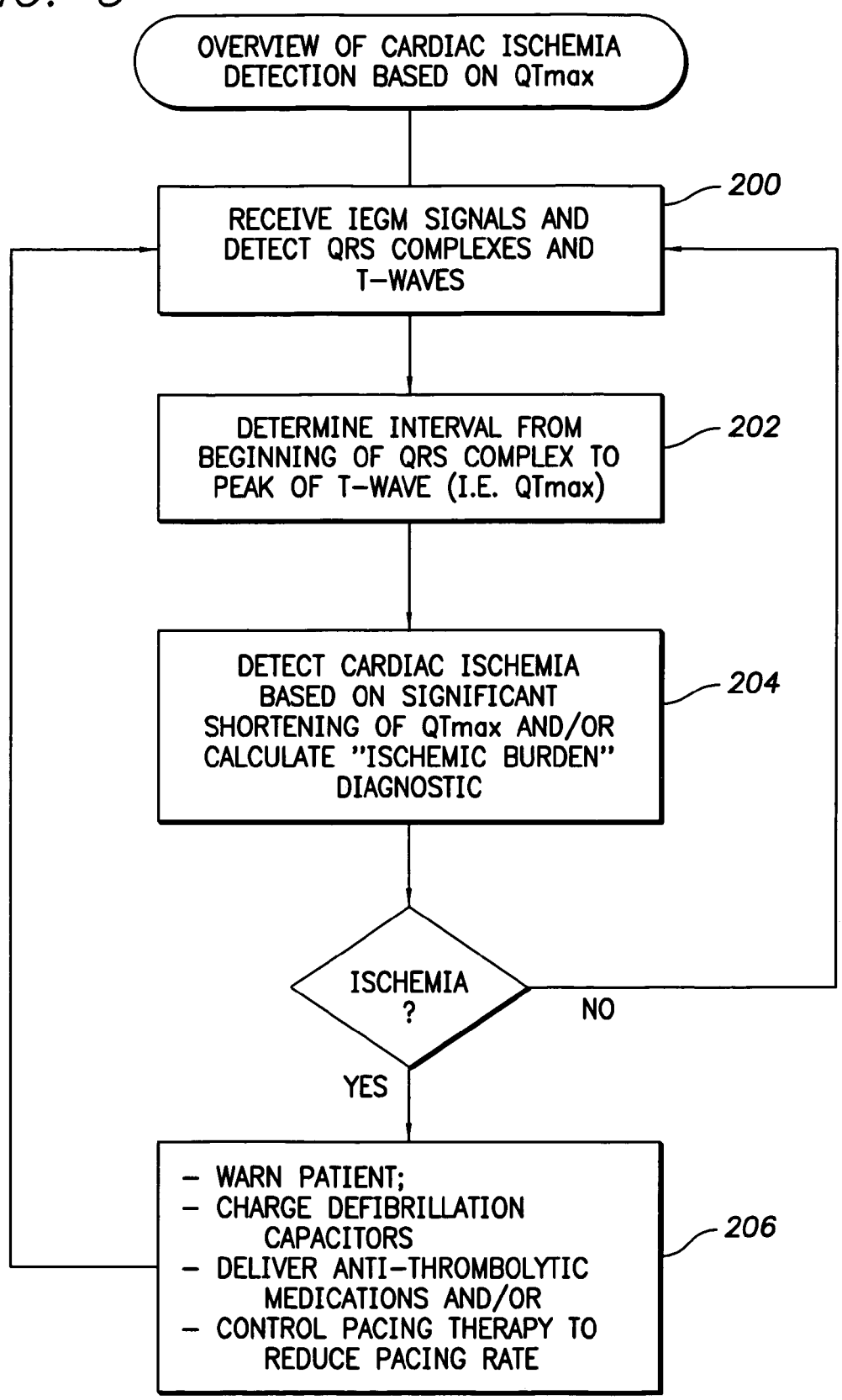
FIG. 3 is a flow chart providing an overview of an exemplary method performed by the device of FIG. 2 for detecting cardiac ischemia based on a reduction in QTmax.

FIG. 3 provides an overview of a QTmax-based cardiac ischemia detection technique performed by the device of FIG. 2. Initially, at step 200, IEGM signals are received and QRS-complexes and T-waves are identified therein. Then, the interval from the beginning of the QRS complex to the peak or maximum absolute amplitude of the T-wave is calculated, at step 202. This interval is referred to herein as QTmax. The Q wave of the QRS complex may be identified as the point within the QRS complex where the IEGM signal exceeds a threshold value set based on the maximum amplitude of the QRS complex itself. The maximum of the T-wave may be identified as the maximum point within a T-wave interval beginning 250 ms following the Q wave of the QRS complex and extending for 200 ms. These are merely exemplary values. At step 204, the onset of a cardiac ischemia is detected based upon detection of a significant shortening of QTmax. Routine experimentation may be performed to determine what constitutes "significant" insofar as changes in QTmax are concerned (and insofar as any other changes referred to herein as being significant are concerned.) In one example, a 10% or greater change in a given parameter is deemed to be significant. Note that QTmax values may be derived from either paced or sensed events but values derived from paced and sensed events should not be combined. In addition, QTmax varies with heart rate and so should be normalized based on heart rate. Bazettte's equation may be used for normalizing QTmax (and for normalizing other parameters discussed herein.) Additionally, or in the alternative, at step 204, the device calculates an "ischemic burden" based on QTmax, which is representative of the proportion of the time ischemia is detected. In one example, the ischemic burden is a numerical value representative of the extent to and/or the time during which QTmax is shorter than its running average. Steps 200–204 are preferably performed once every 30 seconds.

So long as no ischemia is detected, steps 200–204 are merely repeated. If ischemia is detected, however, the patient is warned of the ischemia by application of an internal perceptible "tickle" notification signal, at step 206. If the device is configured to generate warning signals for other conditions, such as hyperglycemia or hypoglycemia, the device preferably employs different notification signal frequencies for the different warnings so that the patient can properly distinguish between different warnings. In addition, warning signals may be transmitted using a short-range telemetry system to a handheld warning device using techniques described within the above-referenced patent application to Wang et al. The handheld warning device thereby provides confirmation of the warning to the patient, who may be otherwise uncertain as to the reason for the internally generated tickle warning signal. Additionally, if so equipped, the device may automatically control therapy in response to the ischemia. For example, if a drug pump is implanted within the patient, the pump may be controlled to deliver suitable anti-thrombolytic medications directly to the patient. Implantable devices for delivering anti-thrombolytic drugs are discussed in U.S. Pat. No. 5,960,797 to Kramer, et al. The device may also change pacing parameters in response to the detection of ischemia to, for example, deactivate overdrive pacing, which may exacerbate the ischemia. Other forms of elevated pacing may be discontinued as well, such as AF suppression therapy or activity-based rate responsive pacing. Various techniques for controlling delivery of therapy in response to ischemia are discussed U.S. Pat. No. 6,256,538 to Ekwall, listed above. See also U.S. Pat. No. 6,377,852 to Bornzin et al., which provides techniques for slowing the heart rate in response to ischemia. In addition, if the device is an ICD, then it may be controlled to immediately begin charging defibrillation capacitors in expectation of delivery of a defibrillation shock, which may be needed if the ischemia triggers VF.

Hence, FIG. 3 provides an overview of technique that seeks to detect the onset of cardiac ischemia based primarily on changes in QTmax. As will be explained below, additional parameters of the IEGM signal, such as ST deviation, may be employed to confirm the detection made based upon to QTmax. Insofar as the detection of T-waves at step 200 is concerned, the invention may exploit techniques set forth in U.S. Patent Application Serial No. 2004/0077962 of Kroll, published Apr. 22, 2004, entitled "System and Method for Monitoring Blood Glucose Levels Using an Implantable Medical Device." Certain techniques described therein are particularly well suited for detecting T-waves with a high degree of accuracy to permit precise detection of features of the T-wave (such as its peak) so as to achieve more precise measurement of QRS/T-wave intervals. The patent application to Kroll is fully incorporated by reference herein. The invention also may exploit T-wave detection techniques set forth within the aforementioned patent application to Min et al., which help prevent P-waves from being misinterpreted as T-waves on unipolar sensing channels.

Figure 4:
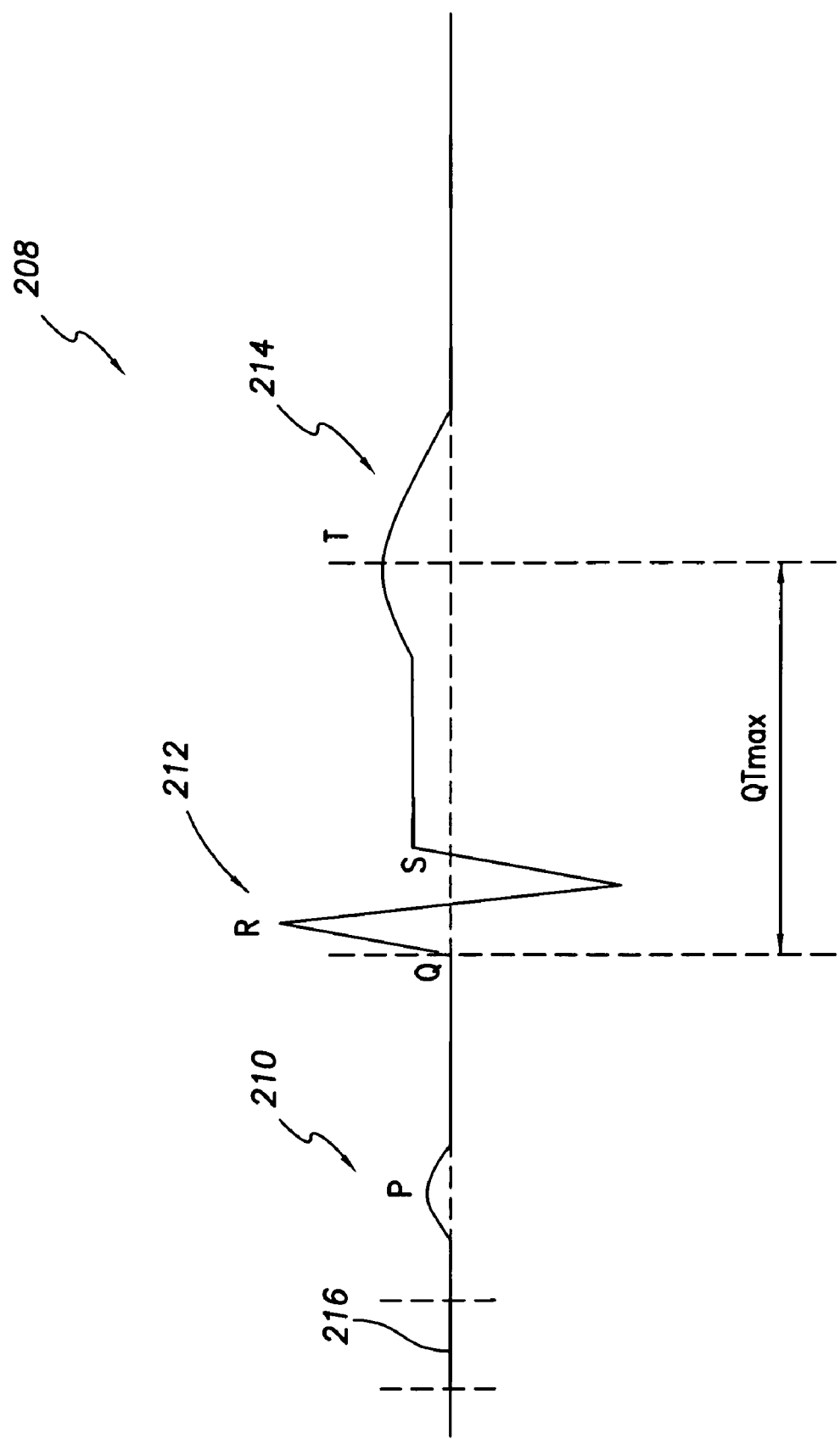
FIG. 4 is a graph providing a stylized representation of the IEGM of a single heartbeat, particularly illustrating the QTmax interval.

FIG. 4 illustrates the QTmax interval. Briefly, the figure provides a stylized representation of an exemplary IEGM trace 208 for a single heartbeat for a patient suffering myocardial ischemia. The stylized representation of the IEGM signal of FIG. 4 is provided for illustrative purposes and should not be construed as an actual, clinically detected IEGM signal. The heartbeat includes a P-wave 210 representative of an atrial depolarization, a QRS complex 212 representative of a ventricular depolarization and a T-wave 214 representative of ventricular repolarization. The QRS complex itself is defined by points Q, R, and S. Q represents the beginning of the complex; R represents the peak of the complex; and S represents the end of the complex. In the examples described and illustrated herein, the aforementioned QTmax interval is specified as the time interval from point Q to the peak or maximum amplitude point of T-wave. However, QTmax may alternatively be calculated based on other points or features of the QRS complex, such as the R point or the S point of the complex, so long as the calculations are consistent. As it is used herein, the "Q" of QTmax generally refers to the QRS complex and not specifically to the Q point of the QRS complex. Hence, the term QTmax encompasses RTmax as one example and STmax as another example. Also, in the particular example of FIG. 4, the peak of the T-wave is positive, i.e. it is greater than a baseline voltage of the IEGM signal. This need not be the case. In other examples, the peak has a negative value with respect to a baseline of the IEGM signal. The polarity of the entire signal may also be reversed. Herein, the peak or maximum amplitude of T-wave refers to the peak or maximum of the absolute value of the difference between the T-wave voltage and the baseline voltage of the IEGM signal. The baseline voltage 216 may be measured during an interval prior to the P-wave, as shown. The interval may be, for example, 50 milliseconds (ms) in duration, beginning 100 ms prior to the P-wave. Alternatively, the interval may be timed relative to the QRS complex. If timed relative to the QRS complex, the interval may commence 250 ms prior to the R wave of the QRS complex. Also alternatively, a single detection point may be used, rather than a detection interval.

Figure 5:
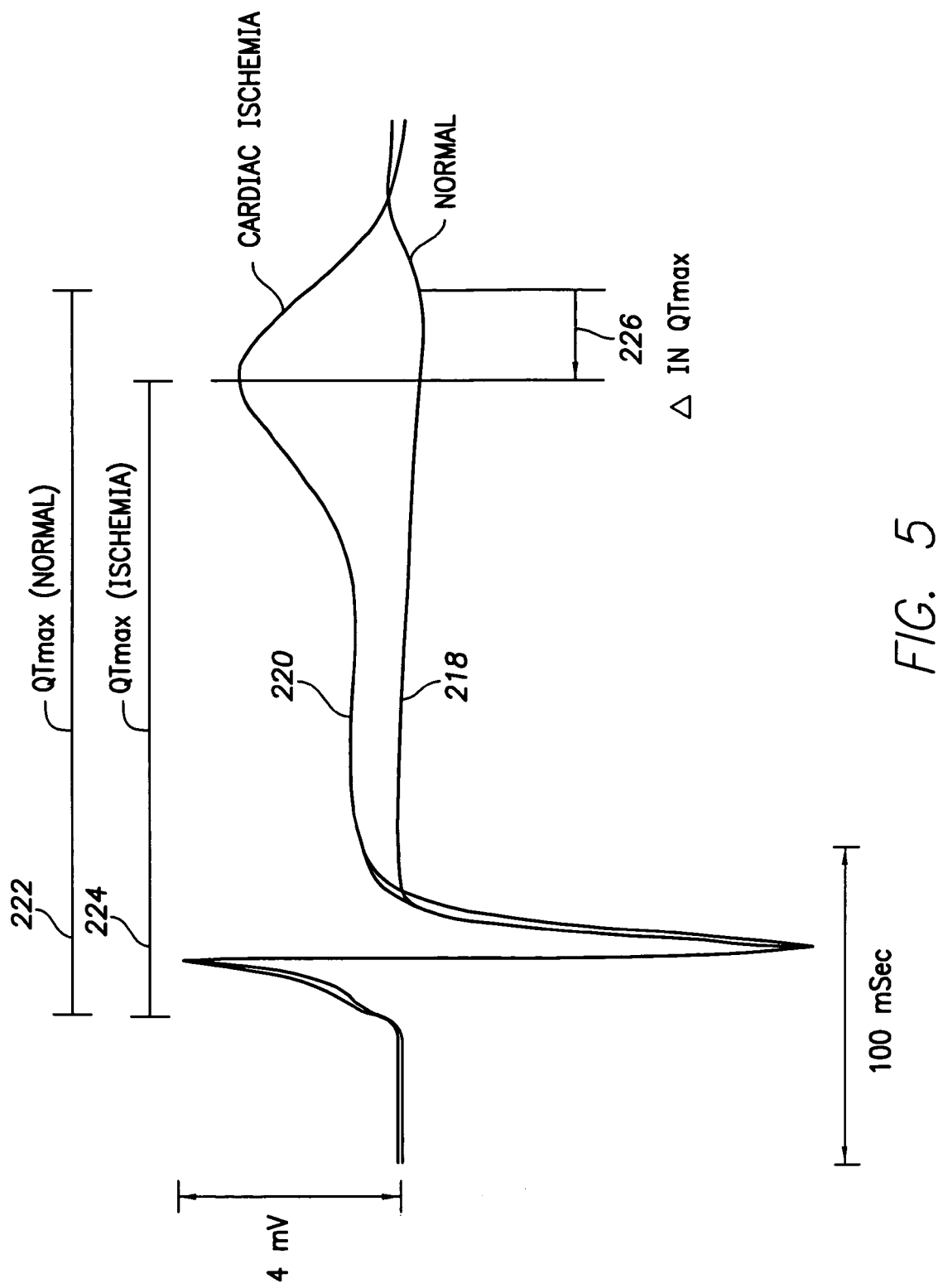
FIG. 5 is a graph providing exemplary representations of the IEGM of a single heart beat, particularly illustrating a reduction in the QTmax interval caused by cardiac ischemia.

FIG. 5 illustrates change in QTmax brought on by acute myocardial ischemia. A first exemplary IEGM trace 218 represents a heartbeat of healthy patient, i.e. one not subject to cardiac ischemia, hypoglycemia or hyperglycemia. A second trace 220 illustrates the heartbeat for a patient suffering an acute myocardial ischemia. The traces are IEGM signals derived from voltage differences between the tip of a right ventricular (RV) lead and the device case. Note first that the IEGM trace for the healthy patient exhibits a T-wave that is reversed in polarity with respect to T-wave of the patient suffering the ischemia. T-wave inversion is typical during ischemia as well as during other conditions such as electrolyte abnormalities, which influence repolarization. Therefore, FIG. 5 illustrates that the QTmax feature is valid even in the presence of a T-wave inversion. In any case, for the purposes of ischemia detection, the peak of the T-wave during ischemia occurs earlier than the corresponding peak without ischemia. In other words, QTmax during ischemia 222 is shorter than QTmax without ischemia 224. Hence, a large positive value of $\Delta$QTmax (226) is observed, where $\Delta$QTmax represents the amount of the reduction in QTmax. A negative value of $\Delta$QTmax is associated with an increase in interval length. In the example FIG. 5, $\Delta$QTmax is represented as a positive number. Note that significant negative $\Delta$QTmax intervals may also be observed which, as will be explained below, are instead indicative of hypoglycemia.

$\Delta$QTmax is the value used to detect the onset of ischemia. Preferably, any change in QTmax from a current baseline value is tracked. In one example, the device tracks a running average of QTmax intervals (derived from sensed events and normalized based on heart rate) for use as a baseline value. Different baseline values may be calculated for different heart rate ranges. In any case, for each new heartbeat, the device compares the QTmax interval for that heartbeat against the appropriate baseline to calculate $\Delta$QTmax for that heartbeat. $\Delta$QTmax values are averaged over, e.g., eight to sixteen heartbeats and then compared against a predetermined QTmax-based threshold. If the average exceeds the threshold, cardiac ischemia is thereby indicated. The threshold is a programmable value set, for example, based upon a percentage of the running average of the QTmax interval. In one specific example, if $\Delta$QTmax is a positive value, which exceeds 10% of the running average of the QTmax intervals, cardiac ischemia is thereby indicated (i.e. QTmax has been found to be reduced by 10%). Otherwise conventional threshold comparison techniques may be employed for use with $\Delta$QTmax. In another example, rather than comparing an average based on eight to sixteen values to the threshold, the occurrence of only a single ΔQTmax value exceeding the threshold is indicative of ischemia. In yet another example, if ΔQTmax exceeds the threshold for three out of five heartbeats, ischemia is indicated. Multiple thresholds may be defined, if desired, to trigger warning signals indicative of different levels of urgency. For example, if ΔQTmax exceeds a first, lower threshold, a warning signal indicative of a moderate ischemia is issued. If ΔQTmax exceeds a higher threshold, a second warning signal indicative of a more serious ischemia is issued. As can be appreciated, a wide variety of specific implementations maybe provided in accordance with the general techniques described herein. Routine experimentation may be performed to determine appropriate threshold levels.

Hence, FIGS. 3–5 provide an overview of techniques for detecting the onset of cardiac ischemia based on changes in the QTmax interval. As will be explained below, particularly with reference to FIG. 13, ST deviation may be used to corroborate any cardiac ischemia detection made based upon QTmax intervals. Other parameters may be used as well to corroborate the detection of cardiac ischemia, including post T-wave-based detection parameters described in the above-referenced patent application to Wang et al. and T-wave energy-based parameters and T-wave slope-based parameters described in the above-referenced patent application Min et al.

Cardiac Ischemia Detection Based on ST Deviation and QTend

Figure 6:
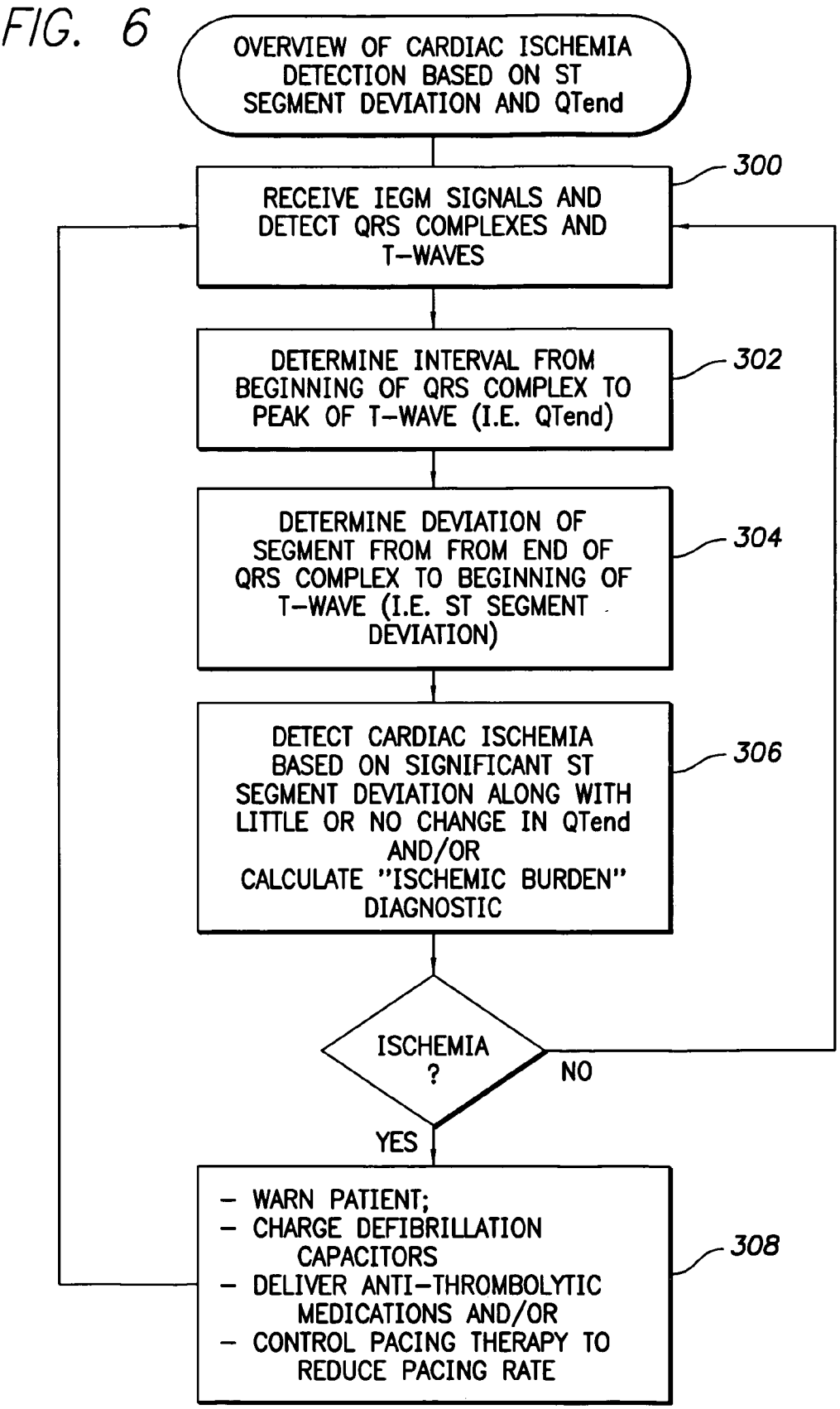
FIG. 6 is a flow chart providing an overview of an exemplary method performed by the device of FIG. 2 for detecting cardiac ischemia based primarily on a significant deviation in the ST segment along with little or no change in the QTend interval.

FIG. 6 provides an overview of a QTend-based cardiac ischemia detection technique performed by the device of FIG. 2. Many aspects of the technique are similar to those of the technique of FIG. 3 and will not be described again in detail. Initially, at step 300, IEGM signals are received and QRS-complexes and T-waves are identified therein. Then, the interval from the beginning of the QRS complex to the end of the T-wave is calculated, at step 302. This interval is referred to herein as QTend. In the examples described and illustrated herein, the QTend interval is specified as the time interval from point Q of the QRS complex to the end point of the T-wave. However, as with QTmax, QTend may alternatively be calculated based on other points or features of the QRS complex, such as the R point or the S point of the complex, so long as the calculations are consistent. The elevation of the interval from the end of the QRS complex to the beginning of the T-wave is also calculated, at step 304. This interval is referred to herein as the ST segment, its elevation is referred to as the ST elevation, and changes in the ST elevation is the ST deviation. Otherwise conventional techniques for detecting ST segment elevation may be used. Detection of ST segment elevation is discussed, for example, in U.S. Pat. Nos. 6,016,443 and 6,256,538 to Ekwall, listed above. At step 306, the onset of a cardiac ischemia is detected based upon observation of a significant deviation in the ST segment along with little or no change in QTend. A deviation in the ST is preferably calculated as a change in the average amplitude of the ST segment. Since the polarity of the IEGM signal is arbitrary, this may, in some cases, represent an increase in voltage of the ST segment and in other cases a decrease in voltage. It is the change in ST segment elevation that is important. As before, data from paced and sensed events should not be combined. QTend values should be normalized based on heart rate. Moreover, ST segments may be referenced beat-by-beat to either the PQ or TP regions of the IEGM.

Additionally, or in the alternative, at step 304, the device calculates an ischemic burden based on ST deviation and QTend, which is representative of the risk of ischemia. In one example, the ischemic burden is a single metric value derived from ST deviation and changes in QTend. Techniques for combining different parameters into a single metric value are set forth in published U.S. Patent Application 2004/0138716, to Koh et al., entitled "System and Method for Detecting Circadian States Using an Implantable Medical Device," published Jul. 15, 2004. If QTend and ST deviation are measured for diagnostic purposes only, steps 300–306 are preferably performed once an hour to calculated and record the ischemic burden. If measured for detecting ischemia, steps 300–306 are preferably performed more often, e.g. once every 30 seconds. In any case, so long as no ischemia is detected, steps 300–306 are merely repeated. If ischemia is detected, however, the patient is warned of the ischemia, at step 308, and, if so equipped, the device automatically controls therapy in response to the ischemia. If the device is an ICD, it may be controlled to immediately begin charging defibrillation capacitors.

Figure 7:
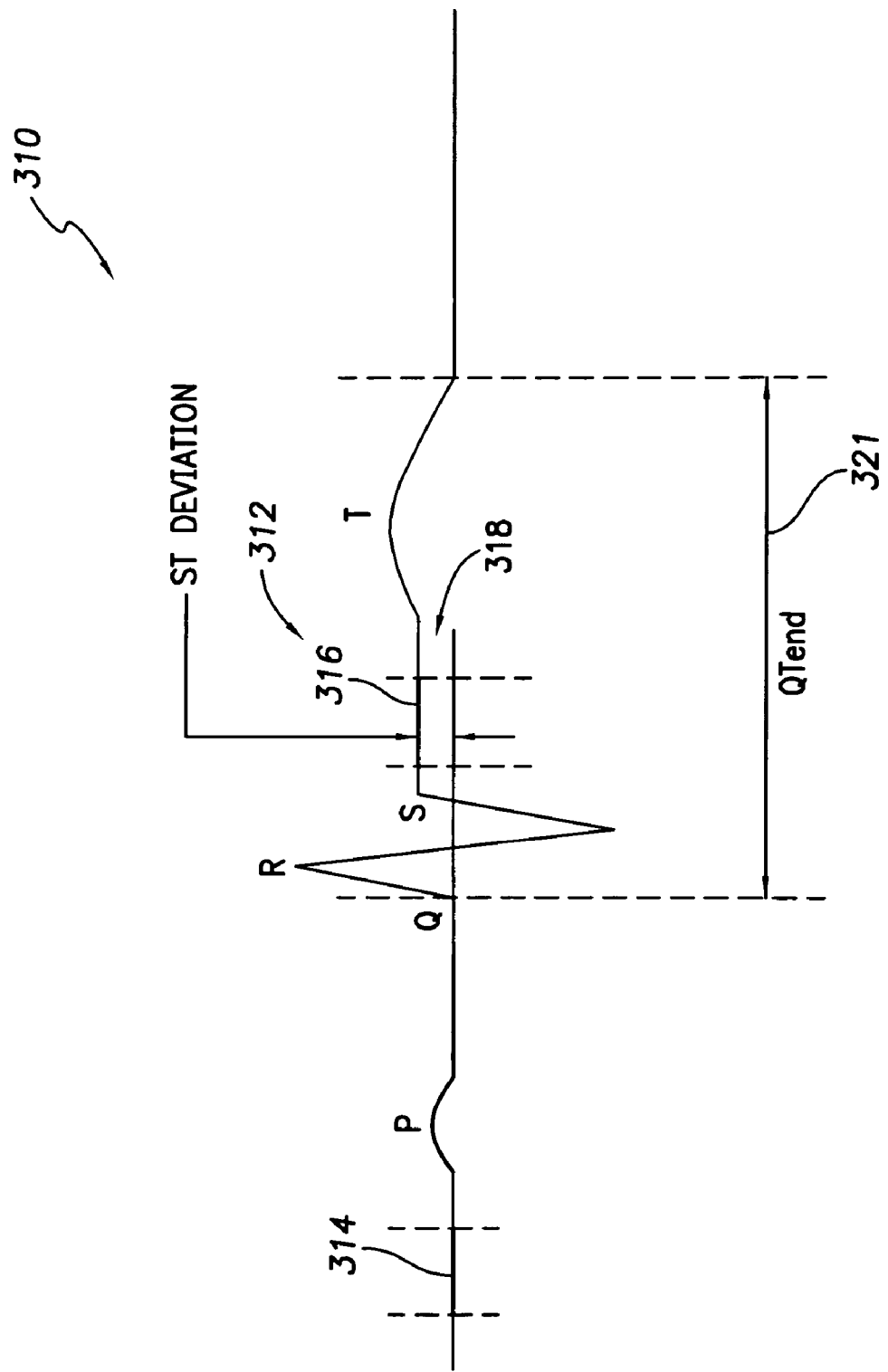
FIG. 7 is a graph providing a stylized representation of the IEGM of a single heartbeat, particularly illustrating ST deviation and the QTend interval.

Hence, FIG. 6 provides an overview of technique that seeks to detect the onset of cardiac ischemia based on a combination of ST deviation and QTend. Additional parameters of the IEGM signal, such as the aforementioned QTmax interval, may be employed to confirm the detection. FIG. 7 illustrates ST segment elevation and the QTend interval. Briefly, FIG. 7 provides a stylized representation of an exemplary IEGM trace 310 for a single heartbeat for a patient suffering a myocardial ischemia. The ST segment 312 is the interval from the end of the QRS complex to the start of the T-wave. The duration of this interval is not of interest in this technique. However, its deviation, i.e. the extent to which its elevation changes over time is of interest. To calculate the elevation of an individual ST segment deviation, the device identifies a window 316 with the ST segment. The elevation of the ST segment (relative to a baseline voltage) within the window is denoted by reference numeral 318. The ST segment elevation may be measured during a specified interval following the QRS complex, as shown. The interval may be, for example, 50 ms in duration, beginning 50 ms following the R wave of the QRS complex. For ventricular paced events, the interval may begin, for example, 80 ms following a V-pulse and extend for 50 ms. These are merely exemplary values. The elevation may be quantified based on the mean of the ST segment sample. Meanwhile, the QTend interval is the time interval between the beginning of the QRS complex and the end point of the T-wave, i.e. the point at which the slope of the T-wave following its peak becomes substantially flat. Techniques for detecting T-wave slope are set forth in the aforementioned patent application to Min et al. The QTend interval is denoted by reference numeral 321.

Figure 8:
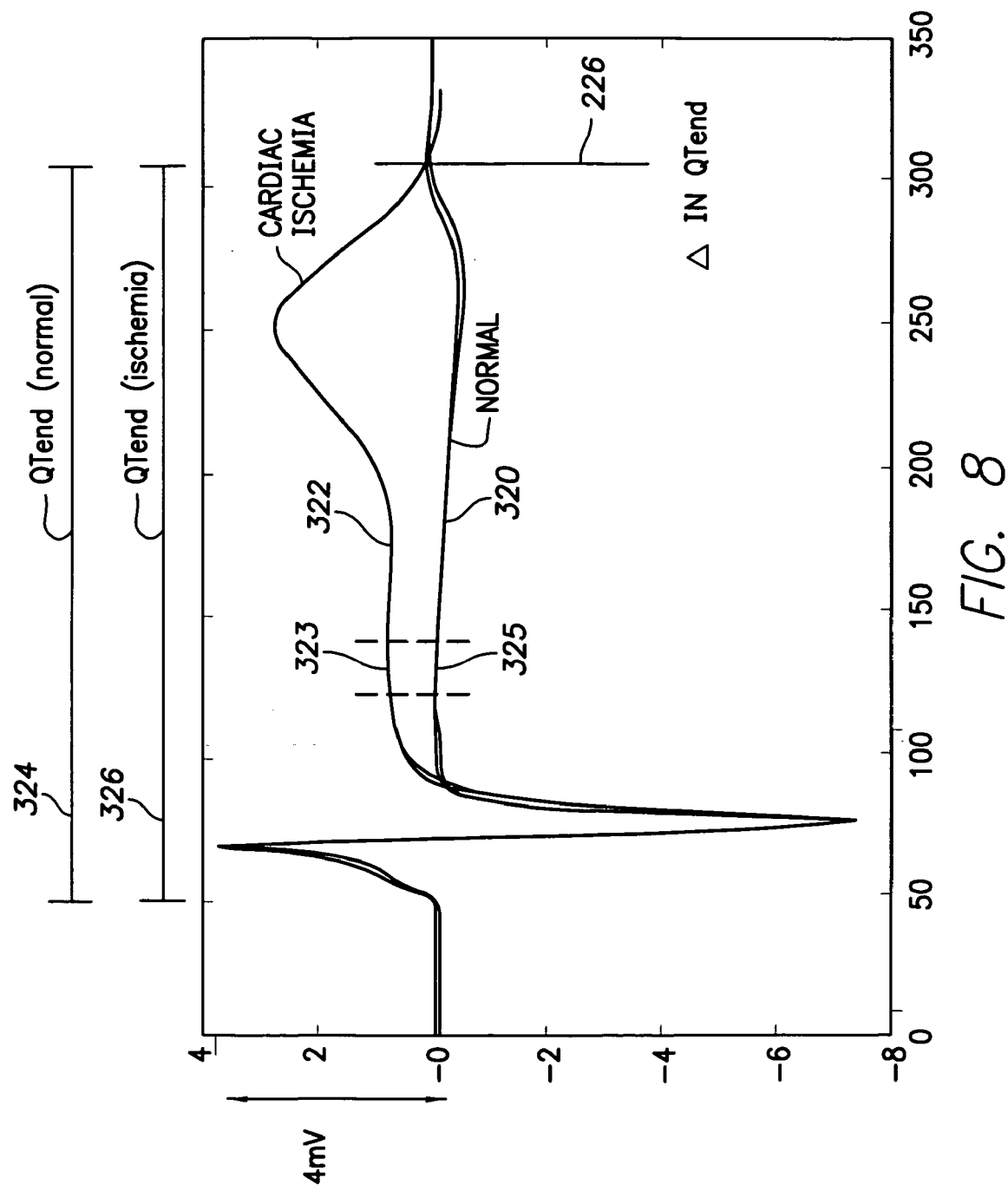
FIG. 8 is a graph providing exemplary representations of the IEGM of a single heart beat, particularly illustrating a significant deviation in the ST segment caused by cardiac ischemia, along with a lack of change in QTend.

FIG. 8 illustrates changes in ST segment elevation brought on by acute myocardial ischemia. A first exemplary IEGM trace 320 represents a heartbeat of a healthy patient, i.e. one not subject to cardiac ischemia or hypo/hyperglycemia. A second trace 322 illustrates the heartbeat for a patient suffering an acute myocardial ischemia. As with other traces illustrated herein, the IEGM signals of FIG. 8 are exemplary representations of IEGM signals provided for illustrative purposes only. Comparing the two traces, the elevation of the ST-segment during ischemia (323) is much greater than the elevation of the ST-segment without ischemia (325), i.e. there is a significant ST deviation. However, there is little or no change in QTend, i.e. the absolute value of □QTend is substantially zero, where ΔQTend represents the amount of the reduction, if any, in QTend interval duration. (A positive value of ΔQTmax is associated with a decrease in interval length. A negative value of ΔQTmax is associated with an increase in interval length. For the purposes of the technique of FIG. 6, only the magnitude of any change in QTend is important.) Hence, QTend helps corroborate the detection of ischemia made based on ST deviation. In particular, as will be explained in more detail below with reference to FIGS. 9–10, a change in ST segment elevation brought on by hypoglycemia will additionally trigger a significant increase in QTend. Hence, without an examination of QTend, it may not be possible to reliably distinguish a change in ST segment elevation caused by ischemia from a change caused by hypoglycemia.

Preferably, any changes in the ST segment elevation and in QTend from current baseline values are tracked. In one example, the device tracks a running average of the ST segment elevation (as derived from sensed events) and then, for each new heartbeat, the device compares the ST segment elevation for that heartbeat against the running average to calculate a ST deviation value for that heartbeat. Note that ST segment values need not be normalized based on heart rate. The device also tracks a running average of the QTend interval (as derived from sensed events and normalized based on heart rate) and then, for each new heartbeat, compares the QTend interval for that heartbeat against the running average to calculate a ΔQTend value for that heartbeat. The value of ST deviation for the heartbeat is averaged over, e.g., eight to sixteen heartbeats and compared against a predetermined deviation-based threshold. If the average exceeds the threshold, then the absolute value of ΔQTend is also averaged over eight to sixteen heartbeats and compared against a predetermined ΔQTend-based threshold. If ST deviation exceeds its respective threshold (indicating a significant change in ST segment elevation), but the absolute value of ΔQTend does not exceed its respective threshold (indicating little or no change in QTend), then cardiac ischemia is thereby indicated. (If ST deviation exceeds its respective threshold and the absolute value of ΔQTend also exceeds its respective threshold, an indication of hypoglycemia may instead be provided. See FIG. 13, discussed below.)

The various thresholds are programmable values set, for example, based upon respective running averages. In one specific example, the threshold for ΔQTend is set to 10% of the running average of the QTend intervals. The threshold for ST deviation may be set, for example, based on some percentage (e.g. 20%) of a running average of peak-to-peak voltage swings in QRS complexes, i.e. based on a percentage of the average difference from a maximum positive voltage to a maximum negative voltage within each QRS complex. Alternatively, the threshold for ST deviation may be set to a preset voltage difference, such as 0.25–0.5 milli-Volts (mV). As with the QTmax-based technique, alternative threshold comparison techniques may instead be used. Multiple thresholds may be defined, in some implementations, to trigger warning signals indicative of different levels of urgency. Routine experimentation may be performed to determine appropriate threshold levels.

Hence, FIGS. 6–8 provide an overview of techniques for detecting the onset of cardiac ischemia based on an examination of ST segment deviation in conjunction with QTend interval. Other parameters may be used to further corroborate the detection of cardiac ischemia, such as the QTmax interval and parameters described in the above-referenced patent applications to Wang et al. and Min et al. In the next section, techniques for detecting hypoglycemia will be described.

Hypoglycemia Detection Based on QTmax and/or QTend

Figure 9:
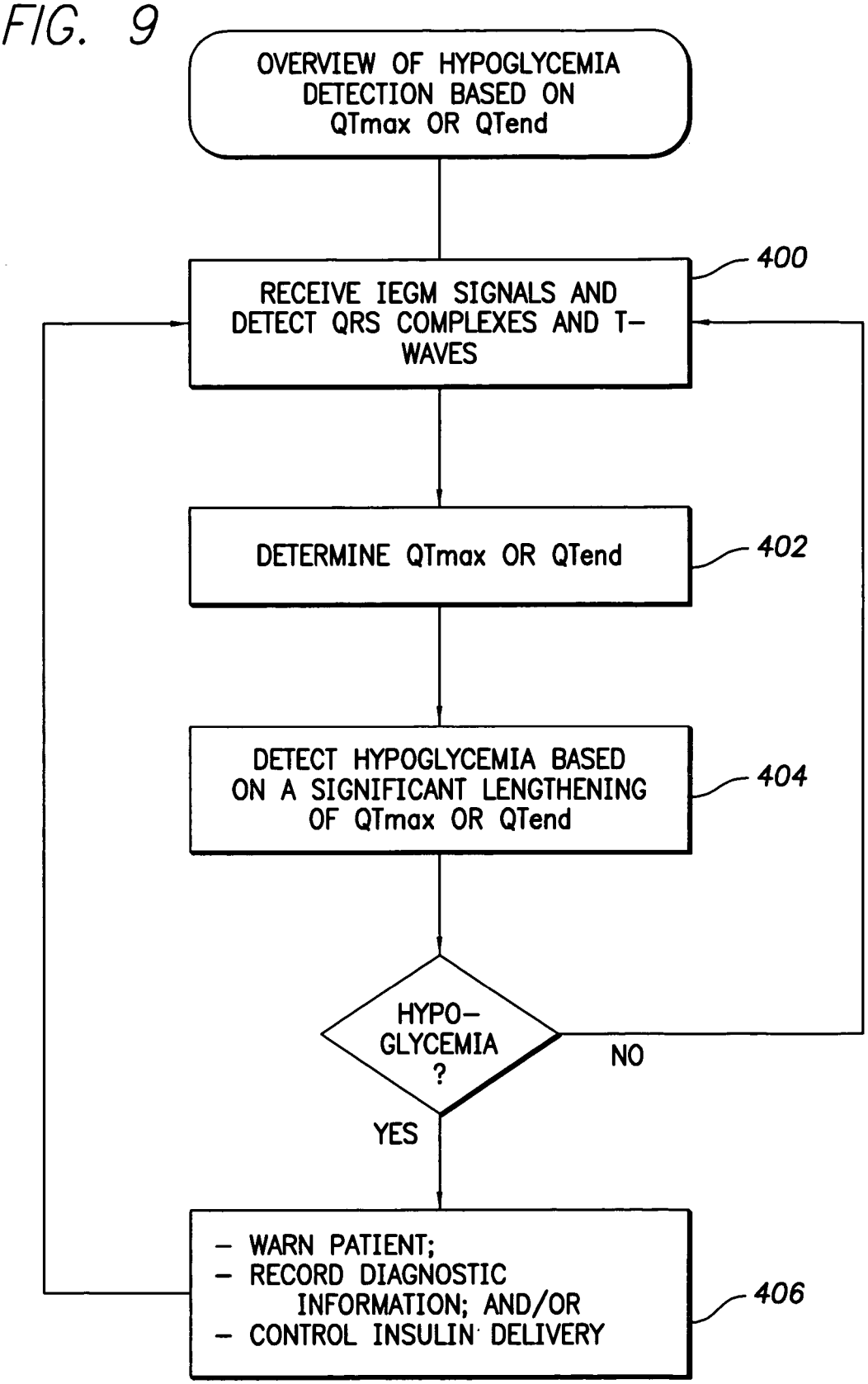
FIG. 9 is a flow chart providing an overview of an exemplary method performed by a hypoglycemia detection system of FIG. 2 for detecting hypoglycemia based primarily on a significant lengthening of either QTmax or QTend.

FIG. 9 provides an overview of hypoglycemia detection techniques performed by the device of FIG. 2. Many aspects of this technique are similar to those of the ischemia detection techniques described above and will not be described again in detail. Initially, at step 400, IEGM signals are received and QRS-complexes and T-waves are identified therein. Then, at step 402, QTmax and QTend intervals are measured. At step 404, the onset of hypoglycemia is detected based upon observation of a significant lengthening of either QTend or QTmax or both. In this regard, both QTmax and QTend increase due to hypoglycemia. Hence, one or the other is sufficient to detect hypoglycemia. Both are preferred to enhance detection reliability. A change in ST segment elevation may be used to further corroborate the detection (see FIG. 13). As before, data from paced or sensed events should not be combined. QTmax and QTend intervals should be normalized based on heart rate.

Additionally, or in the alternative, ST deviation, QTmax and QTend may be stored for diagnostic purposes. The device may calculate a single value representative of the risk of hypoglycemia based on a combination of ST deviation, QTmax and QTend, similar to the ischemic burden discussed above. In any case, so long as hypoglycemia is not detected, steps 400–404 are merely repeated. If hypoglycemia is detected, however, the patient is warned, at step 406. Preferably, the warning signal differs from the one generated for ischemia. If so equipped, the device may automatically initiate therapy appropriate for responding to hypoglycemia. For example, if an insulin pump is implanted within a diabetic patient, the pump may be controlled to adjust the dosage of insulin in response to hypoglycemia. Techniques for controlling delivery of therapy in response to hypoglycemia are set forth in the patent application of Kroll, incorporated by reference above. Information regarding implantable insulin pumps may be found in U.S. Pat. No. 4,731,051 to Fischell and in U.S. Pat. No. 4,947,845 to Davis.

Figure 10:
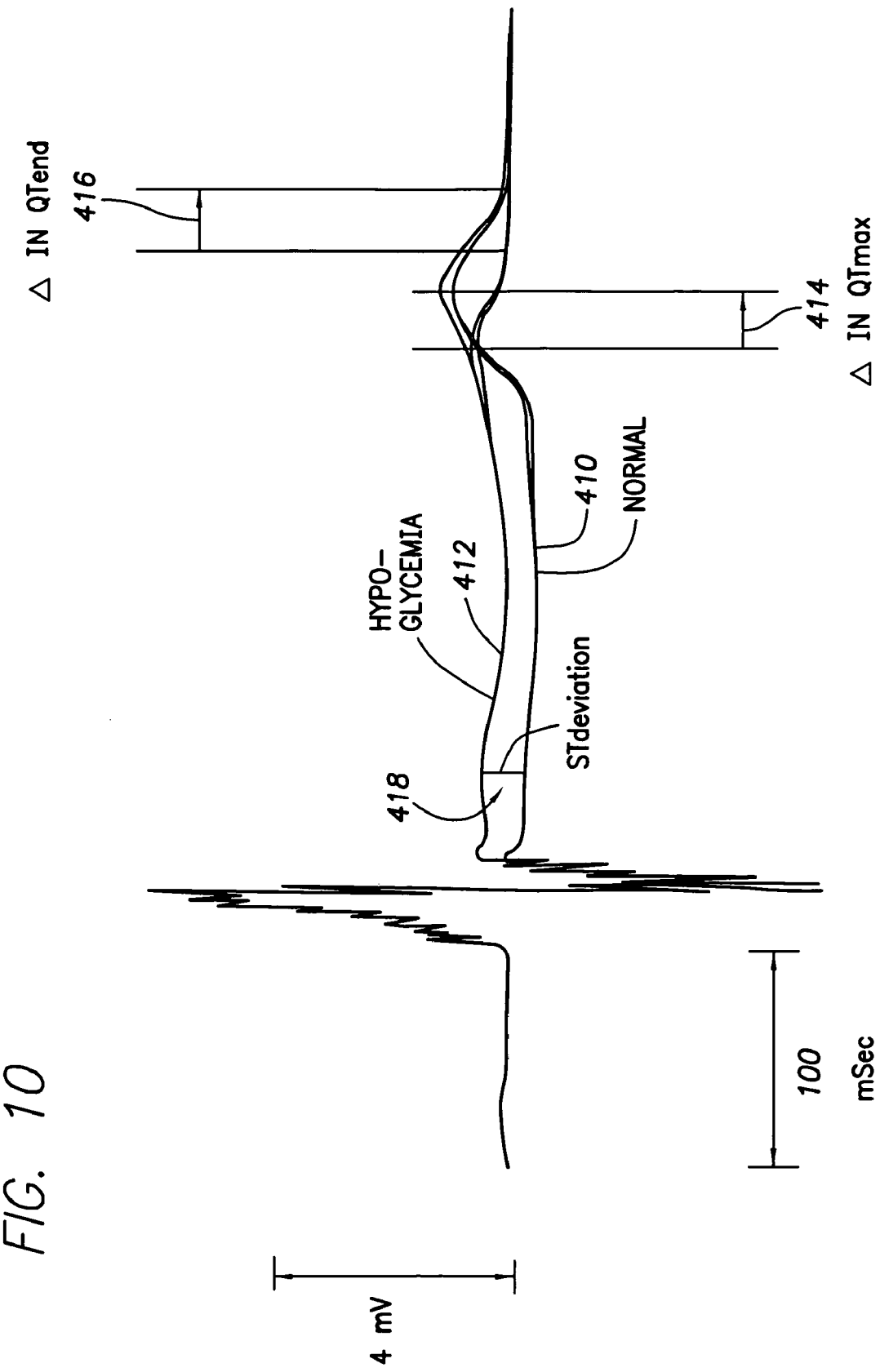
FIG. 10 is a graph providing exemplary representations of the IEGM of a single heartbeat, particularly illustrating a significant lengthening of both QTmax and QTend.

Hence, FIG. 9 provides an overview of technique that seeks to detect the onset of hypoglycemia based on a lengthening of QTmax or QTend. FIG. 10 illustrates QTmax and QTend brought on by hypoglycemia, as well as changes in ST segment deviation. A first exemplary IEGM trace 410 represents a heartbeat of a healthy patient, i.e. one not subject to hypo/hyperglycemia or cardiac ischemia. A second trace 412 illustrates the heartbeat for a patient suffering from hypoglycemia. As with other traces illustrated herein, the IEGM signals of FIG. 10 are exemplary representations of IEGM signals provided for illustrative purposes only. Comparing the two traces, there is a significant lengthening of both QTmax and QTend, i.e. both ΔQTmax and ΔQTend are large in magnitude. (As explained above, ΔQTmax and ΔQTend are defined as positive numbers for a reduction in interval length and as negative numbers for an increase in interval length.)

Hence, an increase in either QTmax or QTend or both allows the device to detect hypoglycemia. ST deviation may be used to corroborate the determination. As can be seen from FIG. 10, the deviation of the ST segment changes in response to hypoglycemia. Preferably, any changes in QTmax and/or QTend are measured with respect to baseline values of those parameters. In one example, the device tracks running averages QTmax and QTend (as derived from sensed events and normalized based on heart rate) fro use as baseline values. Different baseline values may be calculated for different heart rate ranges. Then for each new heartbeat, the device compares new values for those parameters against the appropriate baseline values to calculate ΔQTmax and ΔQTend values for that heartbeat. In the example, the ΔQTmax and ΔQTend values are averaged over eight to sixteen heartbeats. ΔQTmax is compared against a predetermined ΔQTmax-based threshold and ΔQTend is compared against a predetermined ΔQTend-based threshold and. These thresholds may differ in value from the corresponding thresholds discussed above. If ΔQTmax and ΔQTend both exceed their respective thresholds, an indication of hypoglycemia is thereby provided. The various thresholds are programmable values set, for example, based upon percentages of running averages of the respective interval. Again, multiple thresholds may be defined, if desired, to trigger warning signals indicative of different levels of urgency. Routine experimentation may be performed to determine appropriate threshold levels. In the next section, techniques for instead detecting hyperglycemia will be described.

Hyperglycemia Detection Based on ST Deviation, QTmax and QTend

Figure 11:
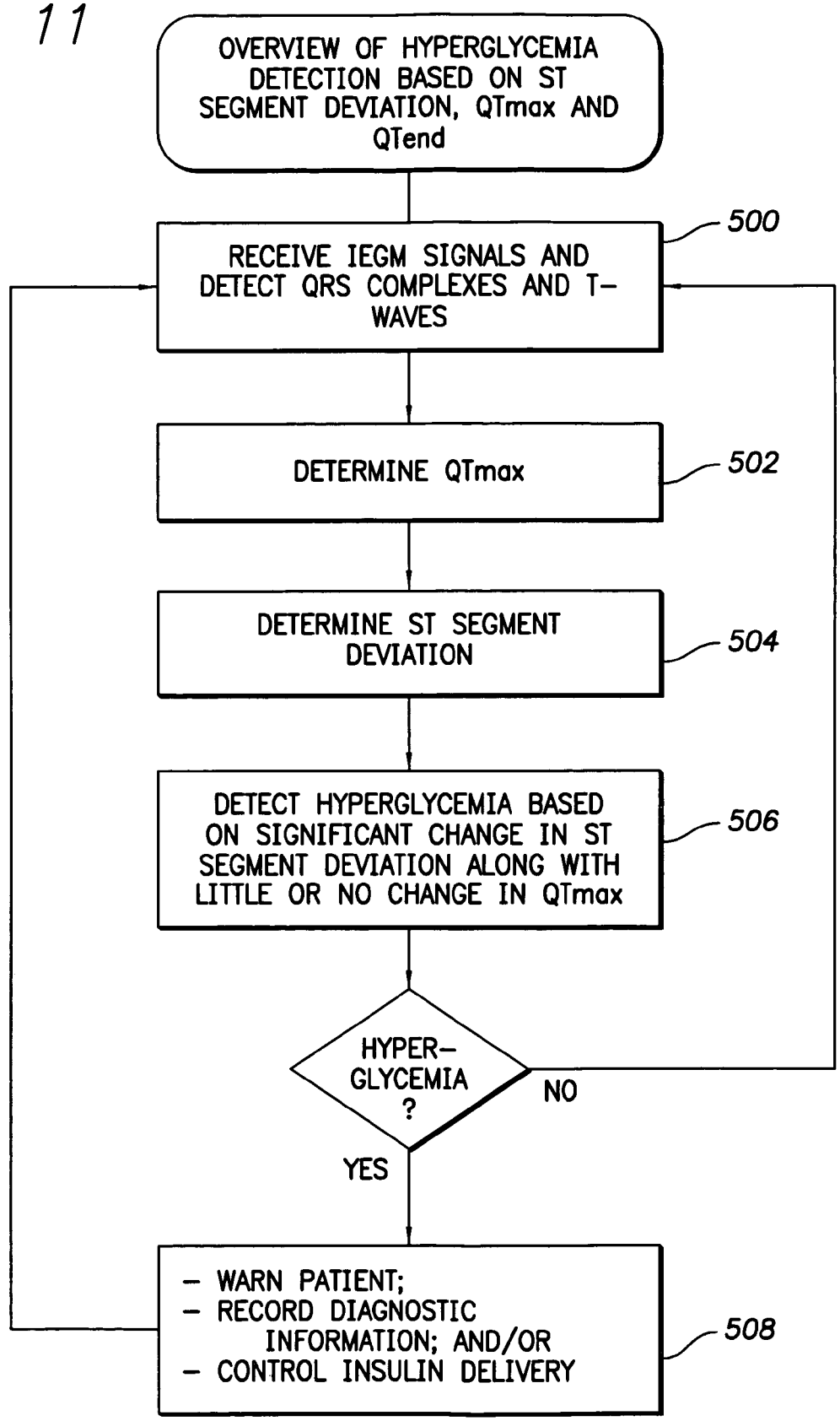
FIG. 11 is a flow chart providing an overview of an exemplary method performed by a hyperglycemia detection system of FIG. 2 for detecting hyperglycemia based primarily on a significant deviation in the ST segment along with little or no change in QTmax.

FIG. 11 provides an overview of hyperglycemia detection techniques performed by the device of FIG. 2. Many aspects of this technique are similar to those of the detection techniques described above and will not be described again in detail. Initially, at step 500, IEGM signals are received and QRS-complexes and T-waves are identified therein. Then, at step 502, QTmax intervals are measured and, at step 504, ST segment elevation is detected. At step 506, the onset of a hyperglycemia is detected based upon detection of a significant change in ST segment elevation along with little or no change in QTmax. A change in ST segment elevation along with a shortening of QTmax is instead indicative of cardiac ischemia. Note that, with hyperglycemia, neither QTmax nor QTend changes significantly. However, a change in ST segment elevation along with little or no change in QTend may also be indicative of either hyperglycemia or cardiac ischemia. So QTmax is observed instead of QTend. As before, data from paced and sensed events should not be combined. QTmax and QTend intervals should be normalized based on heart rate.

Additionally, or in the alternative, values representative of ST deviation, QTmax and QTend may be stored for diagnostic purposes. The device may calculate a single value representative of the risk of hyperglycemia based on a combination of ST deviation, QTmax and QTend, similar to the ischemic burden discussed above. In any case, so long as hyperglycemia is not detected, steps 500–506 are merely repeated. If hyperglycemia is detected, however, the patient is warned, at step 508, and, if properly equipped, the device automatically controls therapy appropriate for responding to hyperglycemia. If an insulin pump is implanted, the pump may be controlled to adjust the dosage of insulin in response to hyperglycemia. Techniques set forth in the patent application of Kroll, listed above, may be suitable for this purpose.

Figure 12:
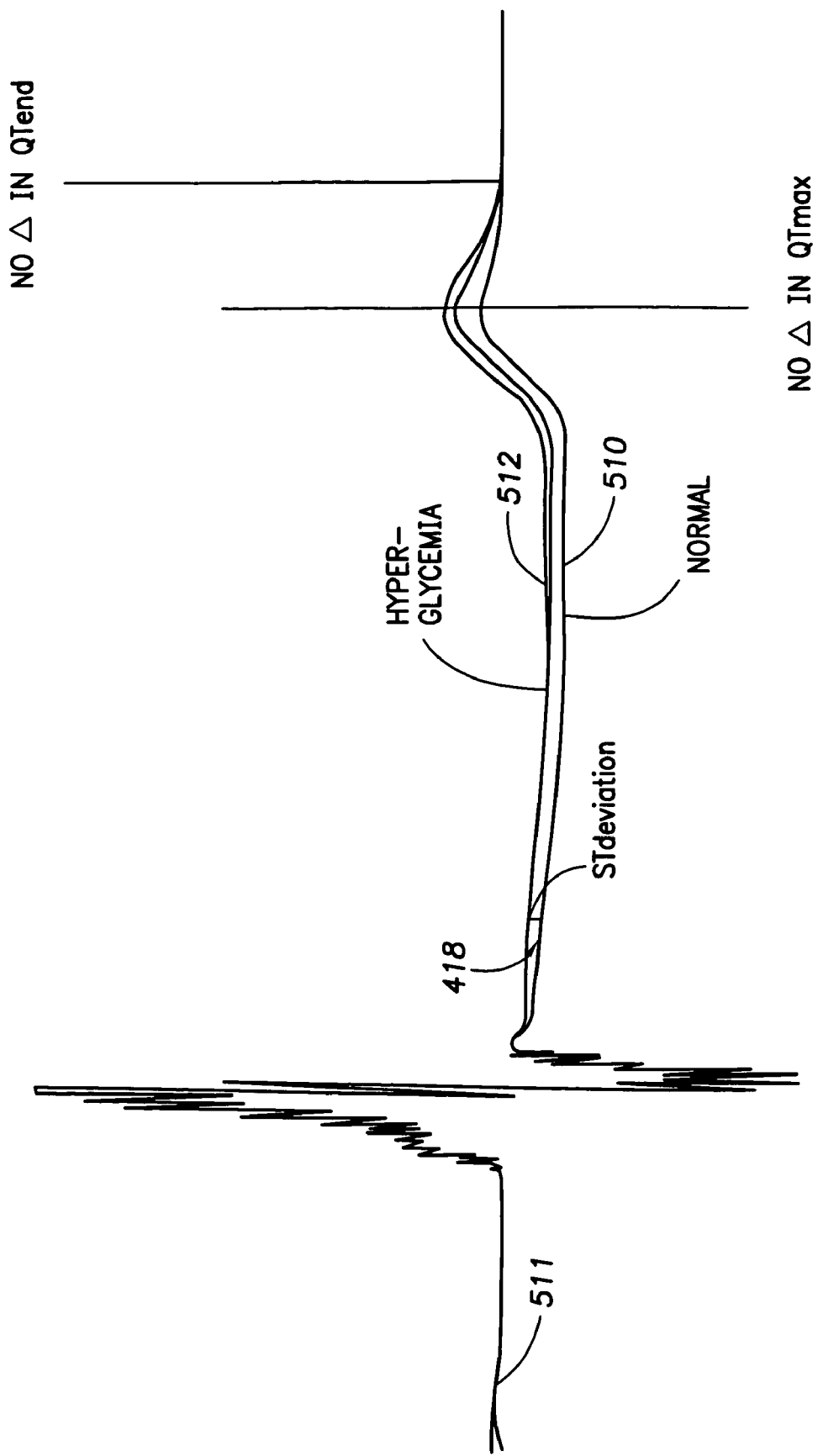
FIG. 12 is a graph providing exemplary representations of the IEGM of a single heart beat, particularly illustrating a significant deviation in ST segment caused by hyperglycemia, along with little or no change in QTmax.

Hence, FIG. 11 provides an overview of a technique that seeks to detect the onset of hyperglycemia based on a combination of ST deviation and QTmax. FIG. 12 illustrates changes in ST segment elevation brought on by hyperglycemia. A first exemplary IEGM trace 510 represents a heartbeat of a healthy patient, i.e. one not subject to hypo/hyperglycemia or cardiac ischemia. A second trace 512 illustrates the heartbeat for a patient with hyperglycemia. As with other traces illustrated herein, the IEGM signals of FIG. 12 are exemplary representations of IEGM signals provided for illustrative purposes only. Comparing the two traces, the elevation of the ST-segment changes. However, there is little or no change in QTmax, i.e. an absolute value of ΔQTmax is near zero. (There is also little or no change in QTend during hyperglycemia, i.e. an absolute value of ΔQTend is also near zero.)

Hence, an examination of QTmax allows the device to properly distinguish a change in ST segment elevation due to hyperglycemia from a change due to hypoglycemia or cardiac ischemia. Compare FIG. 12 with FIGS. 5, 8 and 10, described above. Preferably, any changes in ST segment elevation (as derived from sensed events) and QTmax (as derived from sensed events and normalized based on heart rate) are measured with respect to baseline values of those parameters and values for ST deviation and ΔQTmax are calculated for each heartbeat and averaged over multiple heartbeats. The averaged values are compared against respective thresholds. A warning of hyperglycemia is issued only if ST deviation exceeds its threshold whereas ΔQTmax remains below its thresholds. These thresholds may differ in value from corresponding thresholds discussed above. The various thresholds are programmable values set, for example, based upon respective running averages. Again, multiple thresholds may be defined, in some implementations, to trigger warning signals indicative of different levels of urgency. Routine experimentation may be performed to determine appropriate threshold levels.

What have been described thus far are various techniques for detecting cardiac ischemia, hypoglycemia or hyperglycemia based on various combinations of QTmax, QTend and ST deviation. Preferably, the device is configured to detect any of these conditions and to distinguish therebetween. This is discussed in the following section.

Combined Hypo/Hyperglycemia and Ischemia Detection Examples

Figure 13:
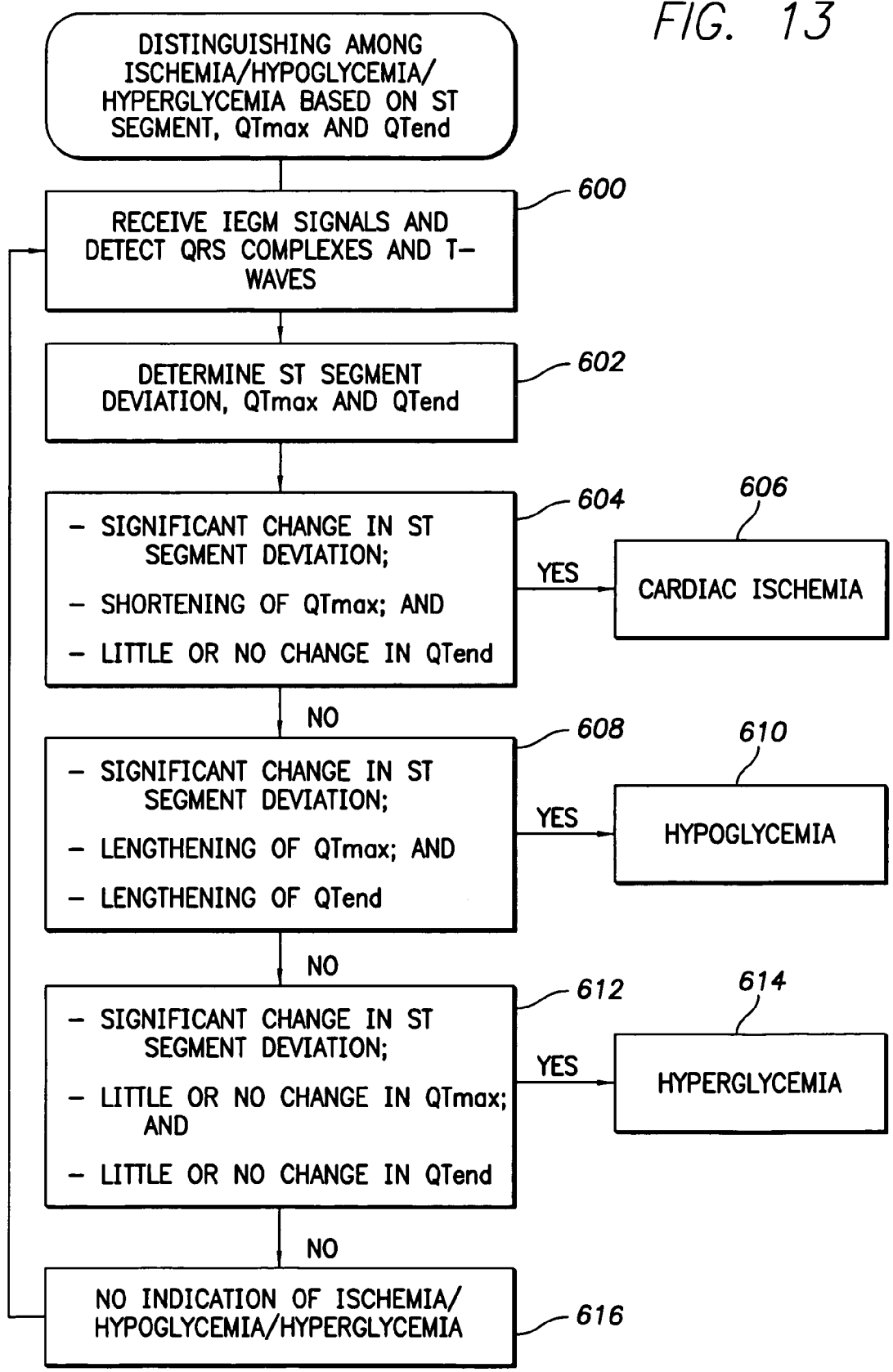
FIG. 13 is a flow chart providing an overview of an exemplary method performed by the implantable device of FIG. 2 for distinguishing among cardiac ischemia, hypoglycemia and hyperglycemia based on ST segment, QTmax, and QTend.

FIG. 13 illustrates an exemplary technique for distinguishing among cardiac ischemia, hypoglycemia and hyperglycemia wherein QTmax, QTend and ST deviation are each examined. Beginning at step 600, the implanted device receives IEGM signals and detect QRS complexes and T-waves. At step 602, the device determines ST segment elevation, QTmax and QTend for each individual heartbeat (as derived from either sensed events only or paced events only and properly normalized based on heart rate). Based upon these values, the device detects and distinguishes between cardiac ischemia, hypoglycemia and hyperglycemia. Briefly, at steps 604–606, the device detects cardiac ischemia based upon any significant change in ST segment elevation (i.e. a significant value for ST deviation) combined with a concurrent shortening of QTmax, so long as there is also little or no change in QTend. At step 608–610, the device detects hypoglycemia based upon any significant change in ST segment elevation combined with a lengthening of both QTmax and QTend. At steps 612–614, the device detects hyperglycemia based upon a significant change in ST segment elevation so long as there is little or no change in either QTmax or QTend. Appropriate warning signals are issued upon detection of ischemia, hypoglycemia or hyperglycemia. The above-described threshold-based techniques may be employed to make these various determinations. Note that the conditions set forth in the steps 604, 608 and 612 are listed above in Table I.

If none of the conditions set forth in steps 604, 608 and 612 are met, then no indication of ischemia, hypoglycemia or hyperglycemia is made, step 616, and processing instead returns to step 604 for examination of additional IEGM signals. In other words, no warning of ischemia, hypoglycemia or hyperglycemia is triggered unless each of the three parameters (ST deviation, QTmax and QTend) corroborates the diagnosis. This differs from the individual examples discussed above wherein an indication of ischemia, hypoglycemia or hyperglycemia may be made based upon significant changes in only one or two of the parameters. By examining all three parameters, a greater degree of reliability and specificity is achieved. Additional detection parameters may be examined as well, including otherwise conventional detection parameters or the parameters set forth in the aforementioned patent applications to Wang et al., and Min et al. IN any case, once the analysis is complete appropriate warnings are issued and therapy is adjusted.

Figure 14:
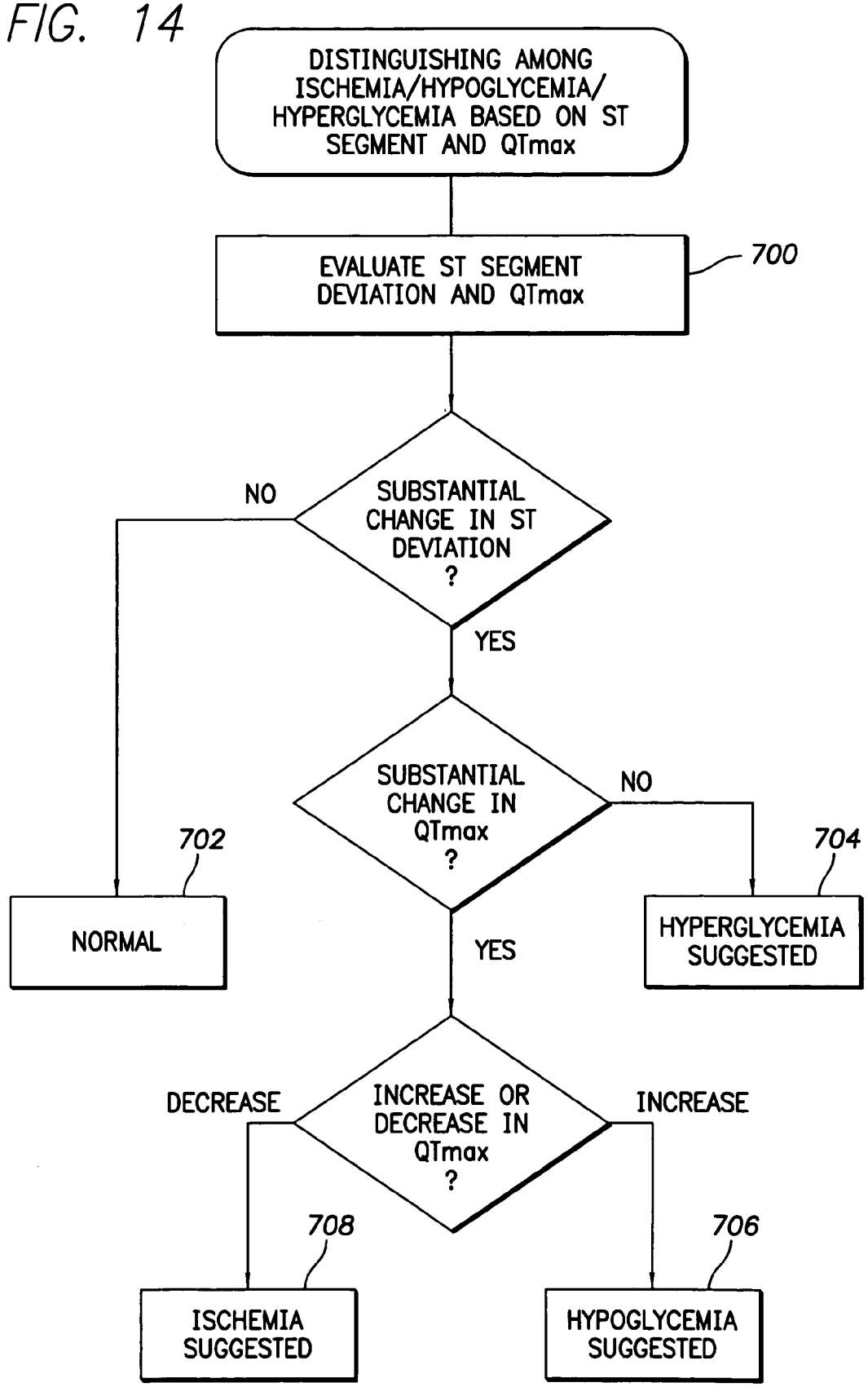
FIG. 14 is a flow chart providing an overview of an exemplary method performed by the implantable device of FIG. 2 for distinguishing among cardiac ischemia, hypoglycemia and hyperglycemia based on ST segment deviation and QTmax.

FIG. 14 illustrates an exemplary technique for distinguishing among cardiac ischemia, hypoglycemia and hyperglycemia based on just QTmax and ST segment elevation. Beginning at step 700, the implanted device evaluates ST segment elevation and ΔQTmax. If there is no substantial change in ST elevation, i.e. ST deviation is small, then the patient's condition is deemed to be normal, at step 702. However, if there has been a substantial change in ST elevation, then the device proceeds to determine whether there has also been a substantial change in QTmax, i.e. whether ΔQTmax exceeds a threshold representative of a significant change. If not, then hyperglycemia is suggested, at step 704. If ΔQTmax exceeds the threshold, however, the device determines whether QTmax has lengthened or shortened. If QTmax has lengthened, then hypoglycemia is suggested that step 706. If QTmax has become shorter, then ischemia is suggested that step 708. The above-described threshold-based techniques may be employed to make these various determinations. Appropriate warning signals are issued and therapy is adjusted.

Figure 15:
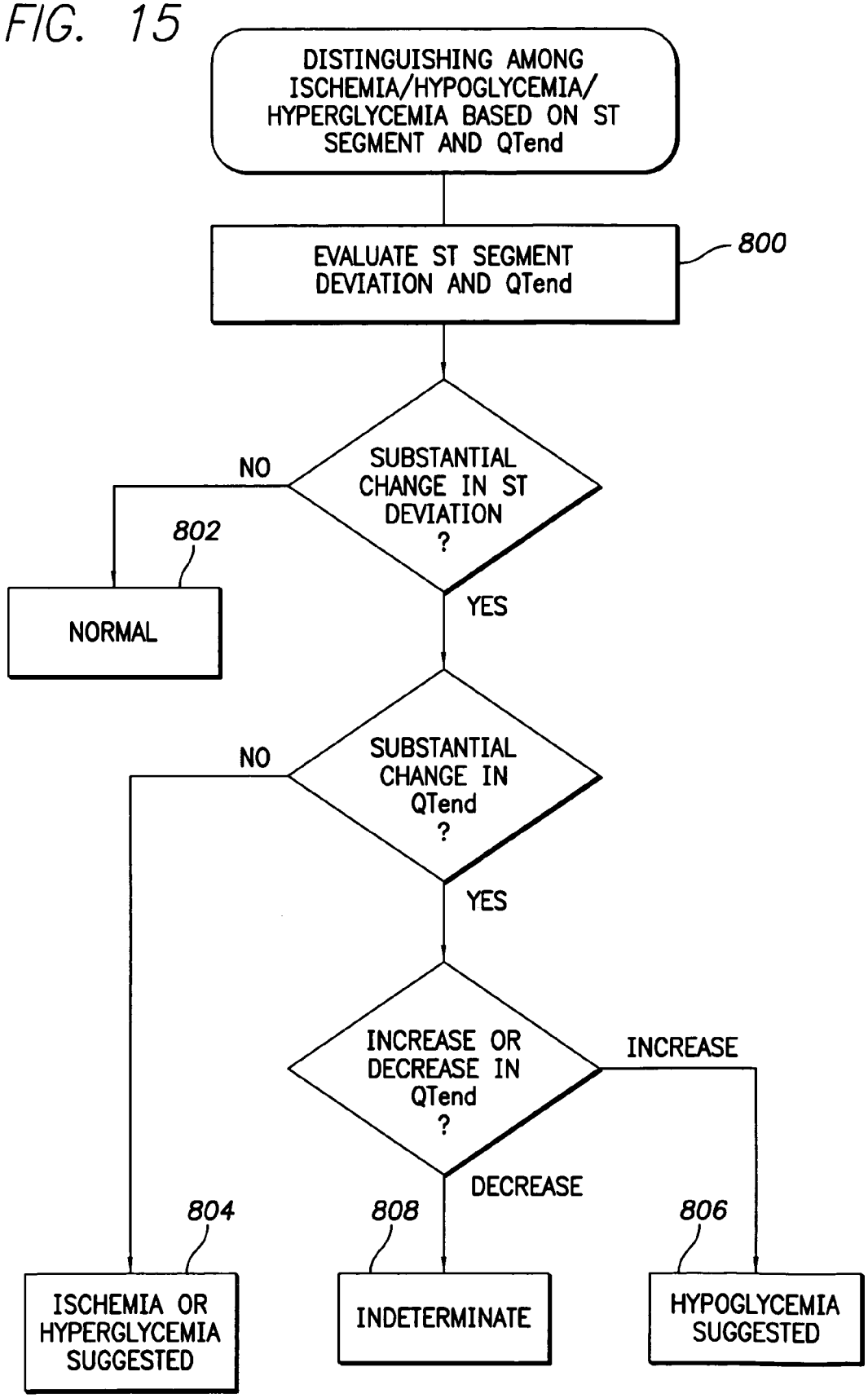
FIG. 15 is a flow chart providing an overview of an exemplary method performed by the implantable device of FIG. 2 for distinguishing among cardiac ischemia, hypoglycemia and hyperglycemia based on ST segment deviation and QTend.

FIG. 15 illustrates an exemplary technique for distinguishing among cardiac ischemia, hypoglycemia and hyperglycemia based on just QTend and ST segment elevation. Beginning at step 800, the implanted device evaluates ST segment elevation and ΔQTend. As before, if there is no substantial change in ST elevation, i.e. ST deviation is small, then the patient's condition is deemed to be normal, at step 802. If there has been a substantial change in ST elevation, then the device proceeds to determine whether there has also been a substantial change in QTend, i.e. whether ΔQTmax exceeds a threshold representative of a significant change. If not, then ischemia or hyperglycemia are suggested, at step 804, and further analysis may need to be performed to distinguish therebetween (such as by examining QTmax). If ΔQTend exceeds the threshold, however, the device then determines whether QTend has lengthened or shortened. If QTend has lengthened, then hypoglycemia is suggested that step 806. If QTend has instead become shorter, then the analysis is indeterminate, at step 808, perhaps indicative of erroneous data. As already explained, a significant change in ST segment elevation in combination with a significant change in QTend should be associated with lengthening of QTend, not a reduction in QTend. Accordingly, no warnings are issued.) Assuming the analysis is not indeterminate, appropriate warning signals are issued and therapy is adjusted.

In general, a wide variety of techniques can be implemented consistent with the principles the invention and no attempt is made herein to describe all possible techniques. Although described primarily with reference to an example wherein the implanted device is a defibrillation/pacer, principles of the invention are applicable to other implantable medical devices as well. In addition, whereas the techniques described herein are performed by the implanted device, the techniques may alternatively be performed by an external device using IEGM signals or other signals transmitted from the implanted device. For example, a bedside monitor may be configured to receive IEGM signals from the implanted device via "long-range" telemetry then analyze the signals using the aforementioned techniques and issue any appropriate warnings. Alternatively, the bedside monitor may transmit the IEGM data to a central server or other central processing device, which analyzes data from multiple patients to detect ischemia, hypoglycemia or hyperglycemia within any of those patients. In such an implementation, the central processing device then transmits appropriate warning signals to the bedside monitor of the patient for warning the patient and then additionally transmits appropriate warning signals to the physician associated with the patient or a third party such as emergency medical service (EMS) personnel. A system incorporating bedside monitoring units connected to a centralized external programmer system is described in U.S. Patent Application Serial No. 2002/0143372, of Snell et al., entitled "System and Method for Remote Programming of Implantable Cardiac Stimulation Devices," published Oct. 3, 2002.

The various functional components of the exemplary systems described herein may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for use with an implantable medical device for detecting hyperglycemia in a patient in which the device is implanted, the method comprising:
   tracking repolarization peak-based intervals representative of intervals between depolarization events and peaks of corresponding repolarization events within electrical cardiac signals;
   tracking repolarization end-based intervals representative of intervals between depolarization events and ends of corresponding repolarization events within electrical cardiac signals;
   tracking elevations of segments of the cardiac signals between depolarization events and corresponding repolarization events; and
   detecting an episode of hyperglycemia based on a change in the elevations of the segments in combination with a lack of change in the repolarization peak-based intervals and the repolarization end-based intervals.

2. The method of claim 1 wherein the repolarization peak-based intervals are representative of intervals between QRS complexes and peaks of corresponding T-waves (QTmax intervals) and wherein the repolarization end-based intervals are representative of intervals between QRS complexes and ends of corresponding T-waves (QTend intervals).

3. The method of claim 1 wherein the segment elevations are representative of the elevations of segments of cardiac signals between QRS-complexes and corresponding T-waves (ST segments).

4. The method of claim 1 further including the step of tracking patient heart rate and wherein the repolarization-peak based intervals and the repolarization-end based intervals are normalized based on heart rate.

5. The method of claim 1 wherein the step of detecting an episode of hyperglycemia based on significant changes in the segment elevations of a plurality of heartbeats compared to a baseline elevation combined with a lack of significant change in repolarization-based intervals of a plurality of heartbeats compared to baseline intervals.

6. The method of claim 1 further including the step of recording diagnostic information representative of the intervals and segment elevations.

7. The method of claim 1 further including the step of controlling therapy in response to the detection of an episode of hyperglycemia.

8. The method of claim 7 wherein an implantable insulin pump is provided and wherein the step of controlling therapy in response to the detection of an episode of hyperglycemia includes the step of controlling insulin delivery to the patient using the insulin pump.

9. The method of claim 1 further including the step of generating a warning signal in response to detection of an episode of hyperglycemia.

10. The method of claim 9 wherein an implantable warning device is provided and wherein the step of generating a warning signal includes the step of delivering a perceptible warning signal to the patient via the implantable warning device.

11. The method of claim 10 for use with an external warning device and wherein the step of generating a warning signal includes the step of transmission control signals to the external warning device for controlling the external device to generate warning signals for warning the patient.

12. A system for use with an implantable medical device for detecting hyperglycemia in a patient in which the device is implanted comprising:
  a timing unit operative to track repolarization peak-based intervals representative of intervals between depolarization events and peaks of corresponding repolarization events within electrical cardiac signals, to track repolarization end-based intervals representative of intervals between depolarization events and ends of corresponding repolarization events within electrical cardiac signals and to track elevations of segments of the cardiac signals between depolarization events and corresponding repolarization events; and
  a hyperglycemia detection unit operative to detect an episode of hyperglycemia based on changes or lack of changes in the elevations of the segments, the repolarization peak-based intervals, and the repolarization end-based intervals.

13. A system for use with an implantable medical device for detecting hyperglycemia in a patient in which the device is implanted comprising:
  means for tracking repolarization peak-based intervals between depolarization events and peaks of corresponding repolarization events within electrical cardiac signals;
  means for tracking repolarization end-based intervals between depolarization events and ends of corresponding repolarization events within electrical cardiac signals;
  means for tracking elevations of segments of the cardiac signals between ends of depolarization events and corresponding repolarization events; and
  means for detecting an episode of hyperglycemia based on changes, if any, in the elevations of the segments, the repolarization peak-based intervals, and the repolarization end-based intervals.

14. A method for use with an implantable medical device for distinguishing among hypoglycemia, hyperglycemia and cardiac ischemia within a patient in which the device is implanted comprising the steps of:
  tracking repolarization-based intervals between depolarization events and corresponding repolarization events within electrical cardiac signals; and
  tracking elevations of segments of the cardiac signals between ends of depolarization events and corresponding repolarization events; and
  distinguishing among hypoglycemia, hyperglycemia and cardiac ischemia based on changes, if any, in the elevations of the segments in combination with changes, if any, in the repolarization-based intervals.

* * * * *